United States Patent
Ikeda et al.

(10) Patent No.: US 12,064,092 B2
(45) Date of Patent: Aug. 20, 2024

(54) CONTROL DEVICE, ENDOSCOPE SYSTEM, AND CONTROL METHOD

(71) Applicant: OLYMPUS CORPORATION, Hachioji (JP)

(72) Inventors: Makoto Ikeda, Hachioji (JP); Ryuhi Okubo, Hachioji (JP); Satoru Adachi, Hachioji (JP); Nana Akahane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 154 days.

(21) Appl. No.: 17/859,439

(22) Filed: Jul. 7, 2022

(65) Prior Publication Data
US 2022/0345608 A1 Oct. 27, 2022

Related U.S. Application Data

(63) Continuation of application No. PCT/JP2020/000353, filed on Jan. 8, 2020.

(51) Int. Cl.
| | |
|---|---|
| *H04N 23/56* | (2023.01) |
| *A61B 1/00* | (2006.01) |
| *A61B 1/045* | (2006.01) |
| *A61B 1/06* | (2006.01) |
| *G02B 23/24* | (2006.01) |
| *H04N 23/72* | (2023.01) |

(Continued)

(52) U.S. Cl.
CPC ........ *A61B 1/0655* (2022.02); *A61B 1/00009* (2013.01); *A61B 1/045* (2013.01); *A61B 1/0638* (2013.01); *G02B 23/2469* (2013.01); *H04N 23/56* (2023.01); *H04N 23/72* (2023.01); *H04N 25/11* (2023.01); *G02B 5/201* (2013.01)

(58) Field of Classification Search
None
See application file for complete search history.

(56) References Cited

U.S. PATENT DOCUMENTS

| | | | |
|---|---|---|---|
| 2006/0232682 A1 | 10/2006 | Ono | |
| 2014/0176783 A1 | 6/2014 | Shibagami | |
| 2016/0273909 A1* | 9/2016 | Nobayashi | ........... H04N 23/672 |

(Continued)

FOREIGN PATENT DOCUMENTS

| | | |
|---|---|---|
| JP | 2006-311505 A | 11/2006 |
| JP | 2014-123070 A | 7/2014 |

(Continued)

OTHER PUBLICATIONS

International Search Report dated Mar. 10, 2020, issued in counterpart International Application No. PCT/JP2020/000353 (2 pages).

*Primary Examiner* — Eileen M Adams
(74) *Attorney, Agent, or Firm* — WHDA, LLP

(57) ABSTRACT

A control device includes: a processor configured to obtain a first picture signal and a second picture signal, calculate first ranging information based on the first picture signal, calculate second ranging information based on the second picture signal, estimate a first subject distance corresponding to the first ranging information, estimate ranging information corresponding to a second focal position, perform arithmetic processing to determine degree of reliability of the first ranging information, and output a result of the arithmetic processing.

14 Claims, 37 Drawing Sheets

(51) Int. Cl.
*H04N 25/11* (2023.01)
*G02B 5/20* (2006.01)

(56) References Cited

U.S. PATENT DOCUMENTS

| | | | |
|---|---|---|---|
| 2017/0199371 A1* | 7/2017 | Williamson | H04N 13/204 |
| 2018/0256017 A1* | 9/2018 | Inoue | G06T 7/73 |
| 2019/0096079 A1* | 3/2019 | Ishibashi | H04N 13/239 |

FOREIGN PATENT DOCUMENTS

| | | |
|---|---|---|
| JP | 2016-142999 A | 8/2016 |
| JP | 2018-128542 A | 8/2018 |

\* cited by examiner

| a1  | a2  | a3  | a4  | a5  |
|-----|-----|-----|-----|-----|
| a6  | a7  | a8  | a9  | a10 |
| a11 | a12 | a13 | a14 | a15 |
| a16 | a17 | a18 | a19 | a20 |
| a21 | a22 | a23 | a24 | a25 |

| N | N | N | N | N |
|---|---|---|---|---|
| N | F | F | F | N |
| N | F | N | N | N |
| N | F | N | F | N |
| N | N | N | N | N |

FIG.17

CONTROL INFINITY END (Far_LMT) — CENTER — PRESENT FOCUS POSITION ▼ — CONTROL NEAR END (Near_LMT)

FIG.26

|  |  | h 1 | h 2 | h 3 | h 4 | h 5 | h 6 | h 7 | h 8 | h 9 | h 10 | h 11 | h 12 | h 13 | h 14 | h 15 |
|---|---|---|---|---|---|---|---|---|---|---|---|---|---|---|---|---|
| READING ROW→ | v 1 | R | ZR | R | G | R | ZR | R | G | R | ZR | R | G | R | ZR | R |
|  | v 2 | G | B | G | B | G | B | G | B | G | B | G | B | G | B | G |
|  | v 3 | R | G | R | G | R | G | R | G | R | G | R | G | R | G | R |
| READING ROW→ | v 4 | G | B | G | B | G | B | G | B | G | B | G | B | G | B | G |
|  | v 5 | R | ZL | R | G | R | ZL | R | G | R | ZL | R | G | R | ZL | R |
|  | v 6 | G | B | G | B | G | B | G | B | G | B | G | B | G | B | G |
|  | v 7 | R | G | R | G | R | G | R | G | R | G | R | G | R | G | R |
| READING ROW→ | v 8 | G | B | G | B | G | B | G | B | G | B | G | B | G | B | G |
|  | v 9 | G | R | R | ZR | R | G | R | ZR | R | G | R | ZR | R | G | R |
|  | v 10 | G | B | G | B | G | B | G | B | G | B | G | B | G | B | G |
|  | v 11 | R | G | R | G | R | G | R | G | R | G | R | G | R | G | R |
| READING ROW→ | v 12 | G | B | G | B | G | B | G | B | G | B | G | B | G | B | G |
|  | v 13 | R | G | R | ZL | R | G | R | ZL | R | G | R | ZL | R | G | R |
|  | v 14 | G | B | G | B | G | B | G | B | G | B | G | B | G | B | G |
|  | v 15 | R | G | R | G | R | G | R | G | R | G | R | G | R | G | R |
| READING ROW→ | v 16 | G | B | G | B | G | B | G | B | G | B | G | B | G | B | G |
|  | v 17 | R | ZR | R | G | R | ZR | R | G | R | ZR | R | G | R | ZR | R |
|  | v 18 | G | B | G | B | G | B | G | B | G | B | G | B | G | B | G |
|  | v 19 | R | G | R | G | R | G | R | G | R | G | R | G | R | G | R |
| READING ROW→ | v 20 | G | B | G | B | G | B | G | B | G | B | G | B | G | B | G |
|  | v 21 | R | ZL | R | G | R | ZL | R | G | R | ZL | R | G | R | ZL | R |
|  | v 22 | G | B | G | B | G | B | G | B | G | B | G | B | G | B | G |
|  | v 23 | R | G | R | G | R | G | R | G | R | G | R | G | R | G | R |
| READING ROW→ | v 24 | G | B | G | B | G | B | G | B | G | B | G | B | G | B | G |
|  | v 25 | G | R | R | ZR | R | G | R | ZR | R | G | R | ZR | R | G | R |

| G | zR | G | Cy | G | zR | G | Cy | G | zR | G | Cy |
|---|----|---|----|---|----|---|----|---|----|---|----|
| Cy | B | Cy | R | Cy | B | Cy | R | Cy | B | Cy | R |
| G | Cy | G | Cy | G | Cy | G | Cy | G | Cy | G | Cy |
| Cy | R | Cy | B | Cy | R | Cy | B | Cy | R | Cy | B |
| G | zL | G | Cy | G | zL | G | Cy | G | zL | G | Cy |
| Cy | B | Cy | R | Cy | B | Cy | R | Cy | B | Cy | R |
| G | Cy | G | Cy | G | Cy | G | Cy | G | Cy | G | Cy |
| Cy | R | Cy | B | Cy | R | Cy | B | Cy | R | Cy | B |
| G | Cy | G | zR | G | Cy | G | zR | G | Cy | G | zR |
| Cy | B | Cy | R | Cy | B | Cy | R | Cy | B | Cy | R |
| G | Cy | G | Cy | G | Cy | G | Cy | G | Cy | G | Cy |
| Cy | R | Cy | B | Cy | R | Cy | B | Cy | R | Cy | B |
| G | Cy | G | zL | G | Cy | G | zL | G | Cy | G | zL |
| Cy | B | Cy | R | Cy | B | Cy | R | Cy | B | Cy | R |
| G | Cy | G | Cy | G | Cy | G | Cy | G | Cy | G | Cy |
| Cy | R | Cy | B | Cy | R | Cy | B | Cy | R | Cy | B |
| G | zR | G | Cy | G | zR | G | Cy | G | zR | G | Cy |
| Cy | B | Cy | R | Cy | B | Cy | R | Cy | B | Cy | R |

FIG.44

FIG.45

CONTROL DEVICE, ENDOSCOPE SYSTEM, AND CONTROL METHOD

CROSS-REFERENCE TO RELATED APPLICATION

This application is a continuation of International Application No. PCT/JP2020/000353, filed on Jan. 8, 2020, the entire contents of which are incorporated herein by reference.

BACKGROUND

1. Technical Field

The present disclosure is related to: a control device to which an endoscope is connected that takes in-vivo images of the inside of a subject when inserted into the subject; an endoscope system; and a control method.

2. Related Art

Regarding the autofocus (AF) control performed using an imaging phase difference detection method; a technology is known that, even under the condition in which the information related to the AF control of a plurality of chronologically-continuous frames needs to be synthesized, enables high-speed processing while maintaining the accuracy of the AF control (for example, refer to Japanese Patent Application Laid-open No. 2016-142999). In this technology, from the pairs of image signals to be used in imaging phase difference detection, the defocusing amount based on the picture-shift amount is calculated along with calculating the degree of reliability of the picture-shift amount. When the degree of reliability is equal to or greater than a predetermined threshold value, AF processing is performed using the defocusing amount. However, when the degree of reliability is not equal to or greater than the predetermined threshold value, AF processing is performed regardless of the defocusing amount. As a result, high-speed processing can be performed while maintaining the accuracy of the AF control.

SUMMARY

In some embodiments, a control device includes: a processor including at least one hardware component. The processor is configured to obtain, in an endoscope device that includes an optical system configured to form an image of a subject, and an imager that includes a phase difference pixel configured to generate a picture signal for generating ranging information correlated to distance from the subject, a first picture signal generated by the phase difference pixel when the optical system has a first optical position, and a second picture signal generated by the phase difference pixel when the optical system has a second optical position, calculate first ranging information based on the first picture signal, calculate second ranging information based on the second picture signal, estimate a first subject distance corresponding to the first ranging information based on reference information indicating correspondence relationship among a distance between the subject and the imager, information indicating focal position of the optical system, and the ranging information, the first ranging information, and information indicating the first focal position, estimate ranging information corresponding to the second focal position based on the estimated first subject distance, information indicating the second focal position, and the reference information, perform arithmetic processing to determine degree of reliability of the first ranging information based on the estimated ranging information corresponding to the second focal position and based on the second ranging information, and output a result of the arithmetic processing.

In some embodiments, an endoscope system includes: an endoscope device; and a control device to which the endoscope device is connected, and that includes a processor including at least one hardware component. The endoscope device includes an optical system configured to form an image of a subject, and an imager that includes a phase difference pixel configured to generate a picture signal for generating ranging information correlated to distance from the subject. The processor is configured to obtain a first picture signal generated by the phase difference pixel when the optical system has a first optical position, and a second picture signal generated by the phase difference pixel when the optical system has a second optical position, calculate first ranging information based on the first picture signal, calculate second ranging information based on the second picture signal, estimate a first subject distance corresponding to the first ranging information based on reference information indicating correspondence relationship among a distance between the subject and the imager, information indicating focal position of the optical system, and the ranging information, the first ranging information, and information indicating the first focal position, estimate ranging information corresponding to the second focal position based on the estimated first subject distance, information indicating the second focal position, and the reference information, perform arithmetic processing to determine degree of reliability of the first ranging information based on the estimated ranging information corresponding to the second focal position and based on the second ranging information, and output a result of the arithmetic processing.

In some embodiments, provided is a control method implemented by a processor including at least one hardware component. The control method includes: obtaining, in an endoscope device that includes an optical system configured to form an image of a subject, and an imager that includes a phase difference pixel configured to generate a picture signal for generating ranging information correlated to distance from the subject, a first picture signal generated by the phase difference pixel when the optical system has a first optical position, and a second picture signal generated by the phase difference pixel when the optical system has a second optical position, calculating first ranging information based on the first picture signal, calculating second ranging information based on the second picture signal, estimating a first subject distance corresponding to the first ranging information based on reference information indicating correspondence relationship among a distance between the subject and the imager, information indicating focal position of the optical system, and the ranging information, the first ranging information, and information indicating the first focal position, estimating ranging information corresponding to the second focal position based on the estimated first subject distance, information indicating the second focal position, and the reference information, performing arithmetic processing to determine degree of reliability of the first ranging information based on the estimated ranging information corresponding to the second focal position and based on the second ranging information, and outputting a result of the arithmetic processing.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 9 is a diagram that schematically illustrates a layout of an imager that includes phase difference pixels;

FIG. 15 is a diagram that schematically illustrates a ranging region in the imager;

FIG. 16 is a diagram that schematically illustrates the focal position direction at each ranging point;

FIG. 17 is a diagram that schematically illustrates the movement direction and the movement amount of a focus lens;

FIG. 26 is a diagram that schematically illustrates a pixel layout of the imager according to a third embodiment;

FIG. 41 is a diagram that schematically illustrates a layout of an imager;

FIGS. 44 and 45 are diagrams that schematically illustrate other layouts of the imager according to the first modification example of the fifth embodiment;

DETAILED DESCRIPTION

Figure 1:
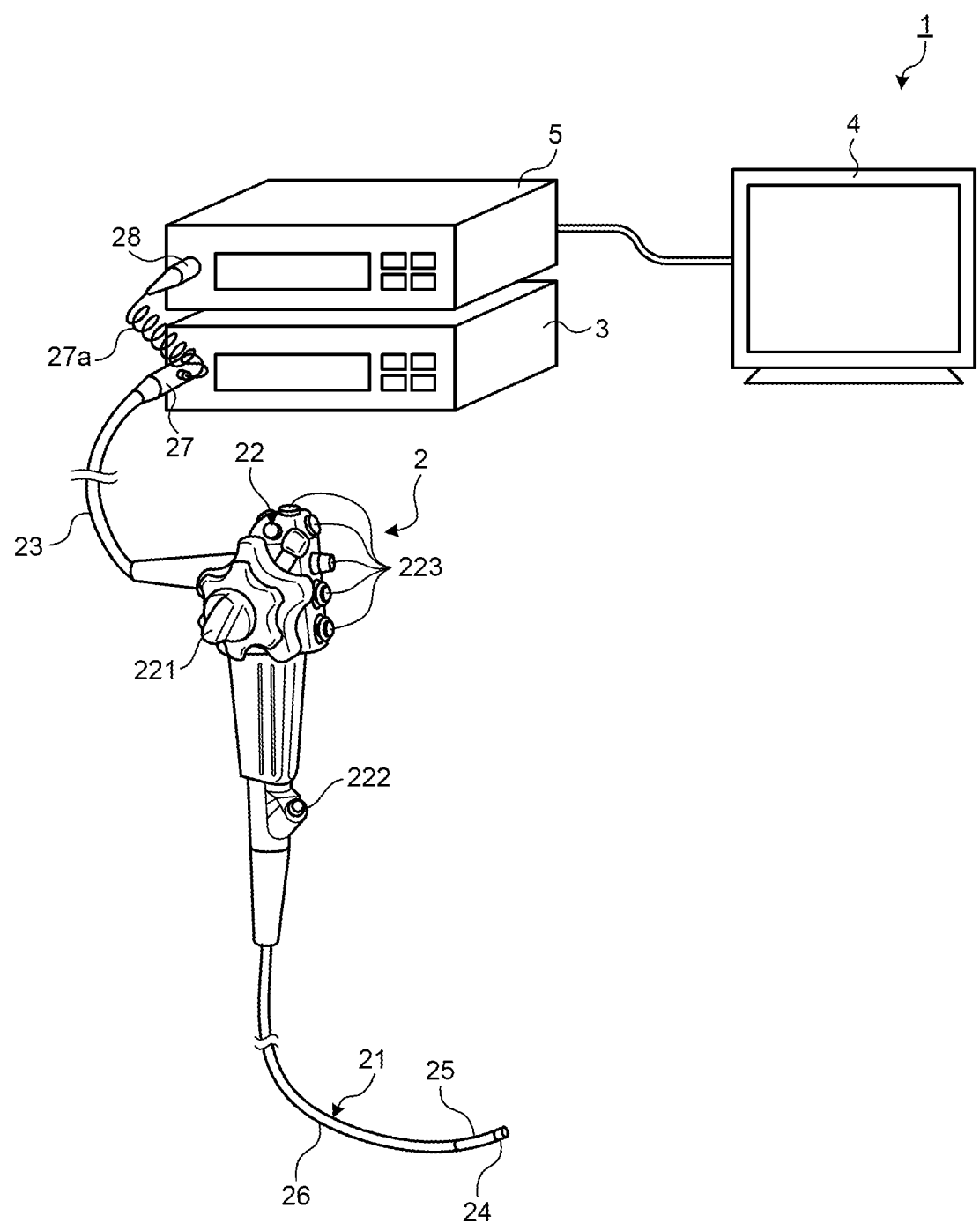
FIG. 1 is an overall configuration diagram illustrating an endoscope system according to a first embodiment.

Exemplary embodiments of the disclosure are described below in detail with reference to the drawings. However, the disclosure is not limited by the embodiments described below. Moreover, in the following explanation given with reference to the drawings; the shapes, the sizes, and the positional relationships are schematically illustrated only to the extent of enabling understanding of the details of the disclosure. That is, the disclosure is not limited to the shapes, the sizes, and the positional relationships illustrated in the drawings.

First Embodiment

Configuration of Endoscope System

Figure 2:
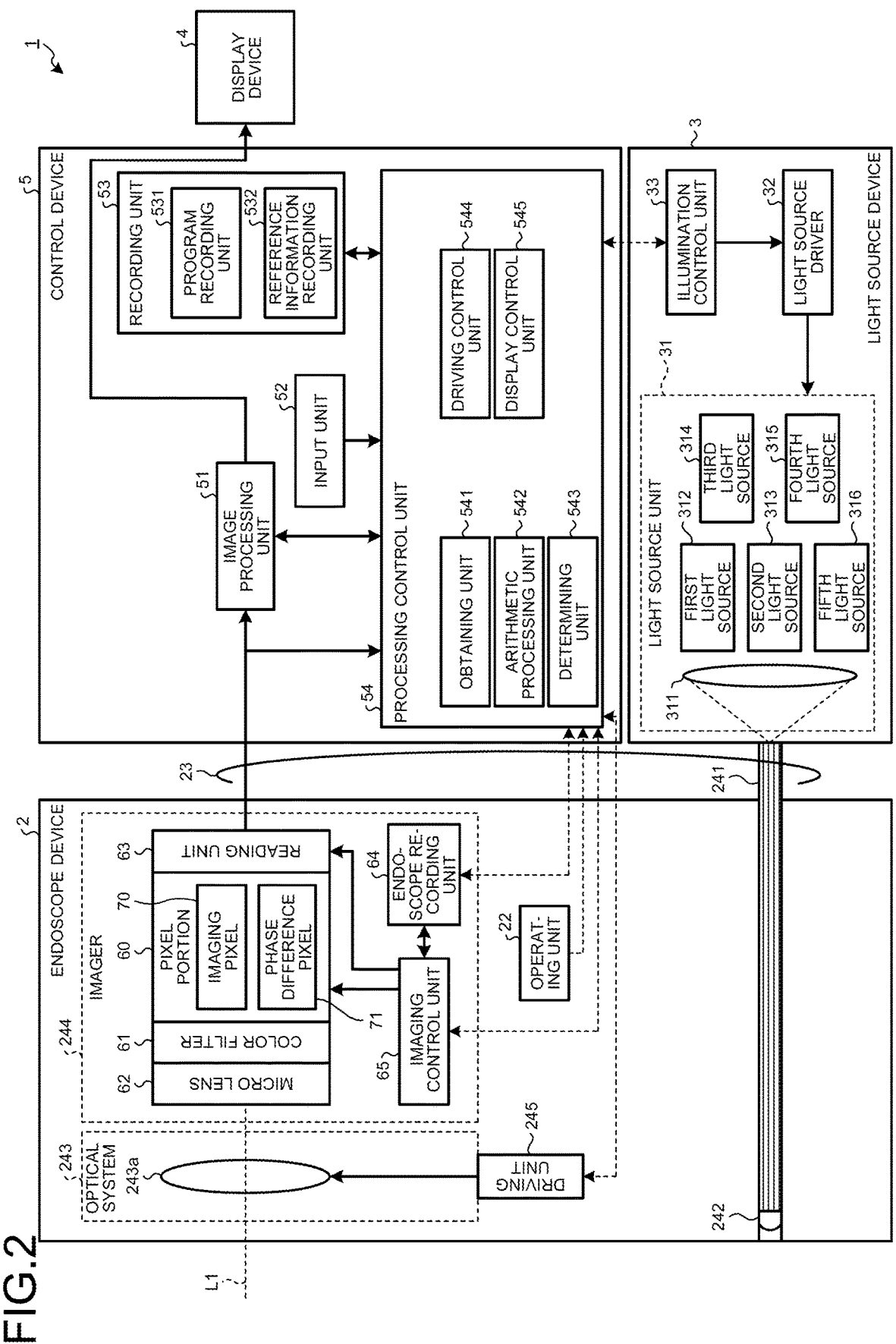
FIG. 2 is a block diagram illustrating a functional configuration of the main parts of the endoscope system according to the first embodiment.

FIG. 1 is an overall configuration diagram illustrating an endoscope system according to a first embodiment. FIG. 2 is a block diagram illustrating a functional configuration of the main parts of the endoscope system according to the first embodiment.

An endoscope system 1 illustrated in FIGS. 1 and 2 takes in-vivo images of a subject, such as a patient, when inserted into the body of the subject, and displays display images based on the taken image data. The user such as a doctor observes the display images and inspects for the presence or absence of a bleeding site, a tumor site, or an abnormal site; and measures the size of such a site. The endoscope system 1 includes an endoscope device 2, a light source device 3, a display device 4, and a control device 5.

Configuration of Endoscope

Firstly, the explanation is given about a configuration the endoscope device 2.

The endoscope device 2 generates image data (RAW data) as a result of capturing the inside of the body of a subject, and outputs the generated image data to the control device 5. The endoscope device 2 includes an insertion portion 21, an operating unit 22, and a universal cord 23.

The insertion portion 21 is flexible in nature and is elongated in shape. The insertion portion 21 includes the following: a front end portion 24 which has an imager 244 (explained later) built-in; a freely-bendable curved portion 25 that is made of a plurality of bent pieces; and a flexible tube 26 that is a flexible tube connected to the proximal end of the curved portion 25.

The front end portion 24 is made of fiberglass, and includes the following: a light guide 241 constituting a light guiding path for the light supplied from the light source device 3; an illumination lens 242 that is disposed at the front end of the light guide 241; an optical system 243 that collects the reflected light coming from the subject; the imager 244 that is disposed at the image formation position of the optical system 243; and a driving unit 245 that moves the optical system 243 along a light axis L1.

The illumination lens 242 is configured using one or more lenses, and directs the light, which is supplied from the light guide 241, to the outside.

The optical system 243 is configured using a plurality of lenses; and collects the reflected light coming from the subject and forms a subject image on the imaging surface of the imager 244. The optical system 243 includes a focus lens 243a that is configured using one or more lenses. The focus lens 243a is disposed to be movable along the light axis L1 and, under the control of the driving unit 245 (explained later), moves along the light axis L1 so that the focal position (the point of focus) of the optical system 243 changes. Meanwhile, a zoom lens group capable of varying the focal length can also be disposed in the optical system 243.

The imager 244 is configured using an image sensor such as a complementary metal oxide semiconductor (CMOS); and performs imaging at a predetermined framerate and outputs image data (PAW data) to the control device 5. The imager 244 includes the following: a pixel portion 60 that is disposed as a two-dimensional matrix; a color filter 61 that is disposed in a laminated manner on the light receiving surface of the pixel portion 60; a micro lens 62 that is disposed on the upper surface of the color filter 61; a reading unit 63; an endoscope recording unit 64 that is used to record a variety of information related to the imager 244; and an imaging control unit 65 that controls the reading unit 63.

The pixel portion 60 includes a plurality of imaging pixels 70 arranged as a two-dimensional matrix, and includes a plurality of phase difference pixels 71 arranged at predetermined intervals and in place of the imaging pixels 70. Each imaging pixel 70 performs photoelectric conversion to generate an image signal corresponding to the light reception amount; and outputs the image signal. Each phase difference pixel 71 is either a right-opening pixel or a left-opening pixel. The phase difference pixels 71 generate a pair of right and left picture signals (phase difference signals) meant for adjustment and distance measurement of the focal position, and output the pair of right and left picture signals. More particularly, each phase difference pixel 71 generates a picture signal to be used for generating ranging information that is correlated to the distance from the subject. Meanwhile, in the image data, image signals and picture signals (phase difference signals) are included.

Configuration of Phase Difference Pixel

Figure 3:
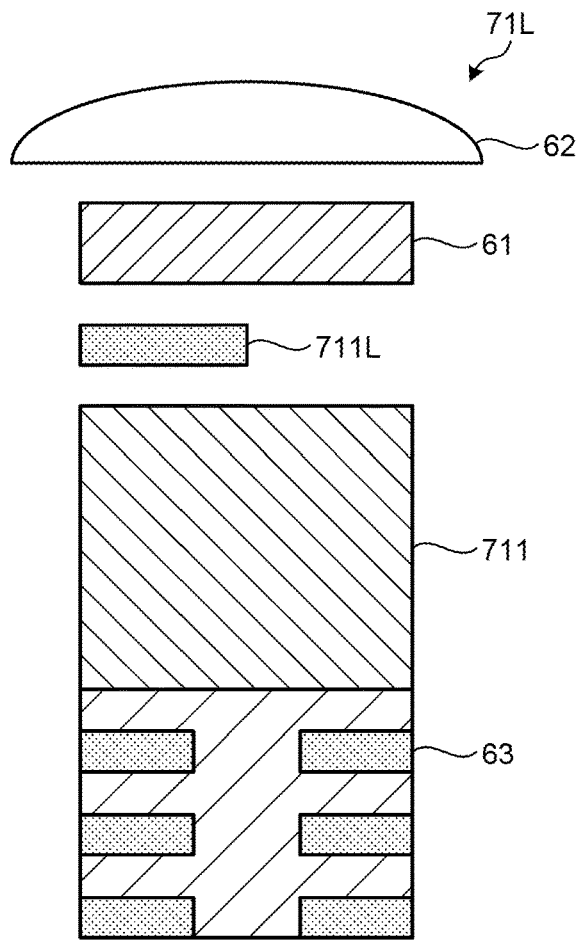
FIG. 3 is a cross-sectional view of a right-opening pixel as a phase difference pixel.
Figure 4:
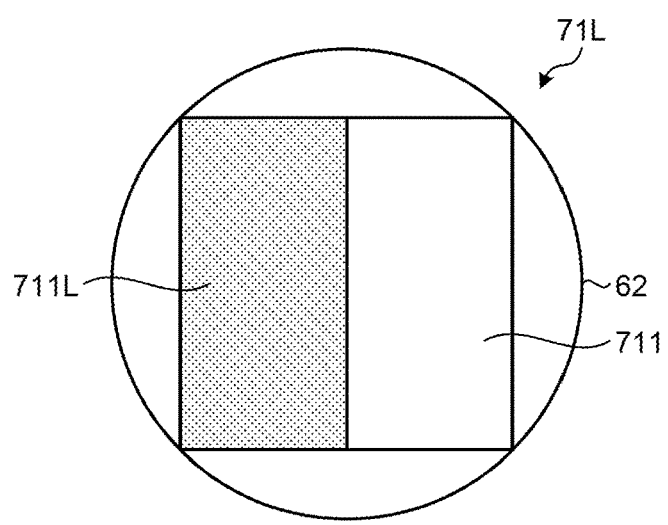
FIG. 4 is a top view of a right-opening pixel as a phase difference pixel.
Figure 5:
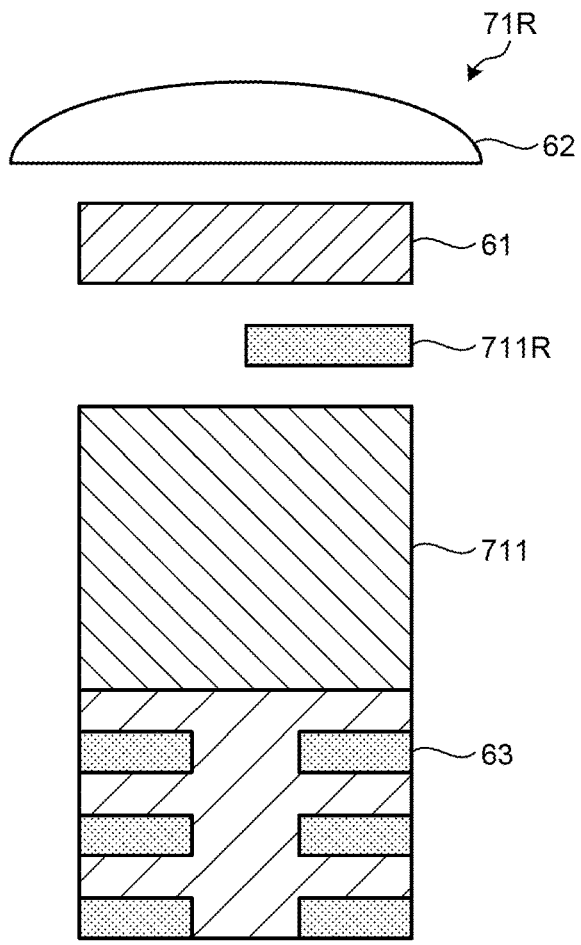
FIG. 5 is a cross-sectional view of a left-opening pixel as a phase difference pixel.
Figure 6:
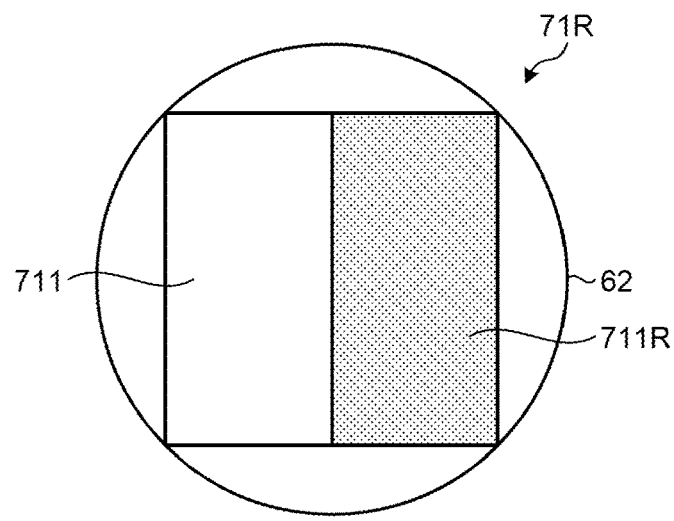
FIG. 6 is a top view of a left-opening pixel as a phase difference pixel.

The following explanation is given about a configuration of the phase difference pixels 71. FIG. 3 is a cross-sectional view of a right-opening pixel as the phase difference pixel 71. FIG. 4 is a top view of a right-opening pixel as the phase difference pixel 71. FIG. 5 is a cross-sectional view of a left-opening pixel as the phase difference pixel 71. FIG. 6 is a top view of a left-opening pixel as the phase difference pixel 71.

Firstly, the explanation is given about a right-opening pixel 71L illustrated in FIGS. 3 and 4.

As illustrated in FIGS. 3 and 4, the right-opening pixel 71L is formed by arranging the following in the given order: a light receiving portion 711 being made of a photodiode and functioning as a photoelectric conversion element; a light shielding portion 711L that is formed on a front surface side of the light receiving portion 711 and that shields the light falling on the left-side region of the light receiving surface; the color filter 61; and the micro lens 62. Moreover, the right-opening pixel 71L is formed by arranging, on a rear surface of the light receiving portion 711, the reading unit 63 that reads electrical signals from the light receiving portion 711.

Given below is the explanation of a left-opening pixel 71R illustrated in FIGS. 5 and 6.

As illustrated in FIGS. 5 and 6, the left-opening pixel 71R is formed by arranging the following in the given order: the light receiving portion 711 being made of a photodiode and functioning as a photoelectric conversion element; a light shielding portion 711R that is formed on the front surface side of the light receiving portion 711 and that shields the light falling on the right-side region of the light receiving surface; the color filter 61; and the micro lens 62. Moreover, the left-opening pixel 71R is formed by arranging the reading unit 63 on the rear surface side of the light receiving surface.

The right-opening pixels 71L and the left-opening pixels 71R configured in the manner explained above generate pairs of right and left picture signals meant for adjustment and distance measurement of the focal position.

Configuration of Color Filter

Figure 7:
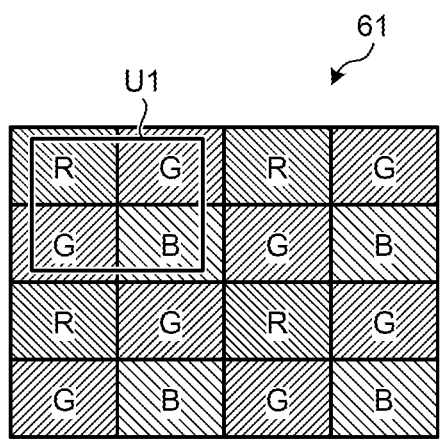
FIG. 7 is a diagram that schematically illustrates a layout of a color filter.

Given below is the explanation of a configuration of the color filter 61. FIG. 7 is a diagram that schematically illustrates a layout of the color filter 61.

The color filter 61 illustrated in FIG. 7 is made of 2×2 filter units U1. In the color filter 61, of a plurality of filters, each filter is placed on the light receiving surface of either the imaging pixel 70, or the light receiving portion 711 of the right-opening pixel 71L, or the light receiving portion 711 of the left-opening pixel 71R. Each filter unit U1 is configured using the Bayer layout; and is made of a red filter R that transmits the light having the wavelength bandwidth of the red color, a green filter G that transmits the light having the wavelength bandwidth of the green color, and a blue filter B that transmits the light having the wavelength bandwidth of the blue color.

Figure 8:
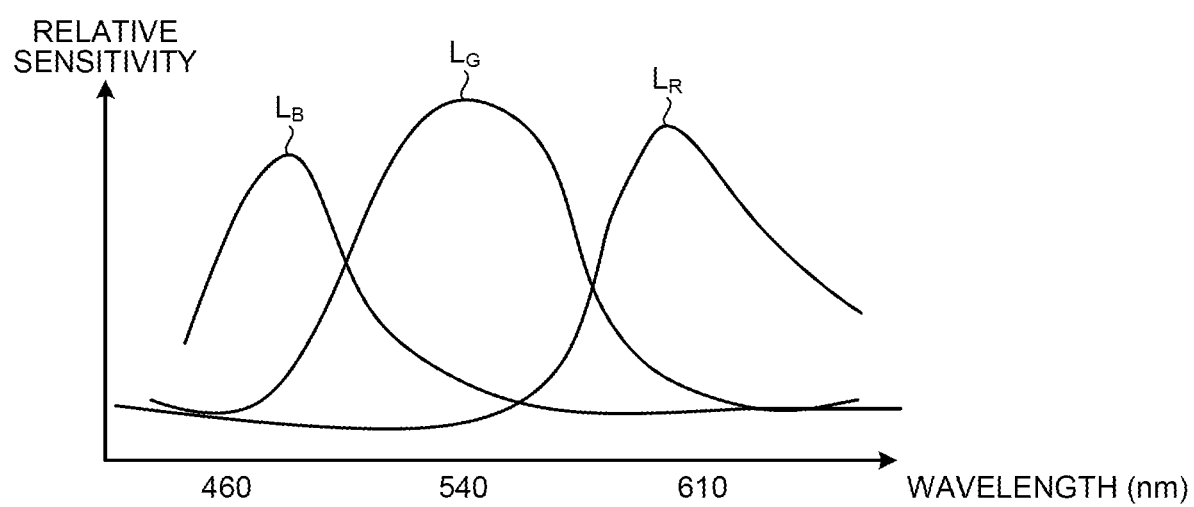
FIG. 8 is a diagram that schematically illustrates the sensitivity and the wavelength bandwidth of each filter.

FIG. 8 is a diagram that schematically illustrates the sensitivity and the wavelength bandwidth of each filter. In FIG. 8, the horizontal axis represents the wavelength (nm), and the vertical axis represents the sensitivity. Moreover, in FIG. 8, a curved line $L_B$ indicates the sensitivity of the blue filter B, a curved line $L_G$ indicates the sensitivity of the green filter G, and a curved line $L_R$ indicates the sensitivity of the red filter R.

As illustrated in FIG. 8, the blue filter B transmits the light having the wavelength bandwidth of the blue color. The green filter G transmits the light having the wavelength bandwidth of the green color. The filter R transmits the light having the wavelength bandwidth of the red color. In the following explanation, the imaging pixel 70 having the red filter R disposed on the light receiving surface thereof is referred to as an R pixel; the imaging pixel 70 having the green filter G disposed on the light receiving surface thereof is referred to as a G pixel; and the imaging pixel 70 having the blue filter B disposed on the light receiving surface thereof is referred to as a B pixel. Moreover, the right-opening pixels 71L from among the phase difference pixels 71 are referred to as zR pixels, and the left-opening pixels 71R from among the phase difference pixels 71 are referred to as zL pixels.

Figure 9:
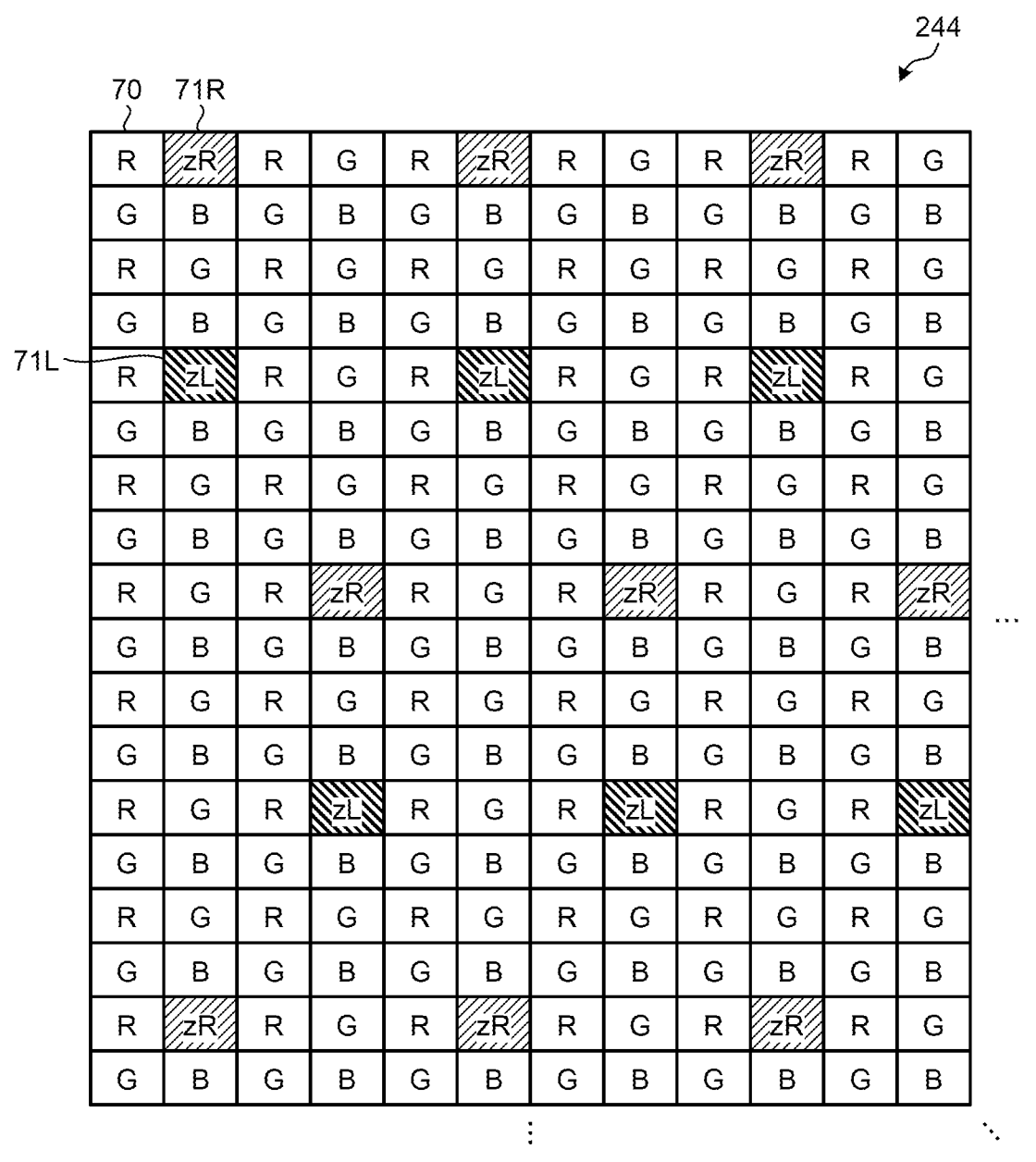

Given below is the explanation of the layout of the imager 244 that includes the phase difference pixels 71. FIG. 9 is a diagram that schematically illustrates a layout of the imager 244 that includes the phase difference pixels 71.

As illustrated in FIG. 9, one right-opening pixel 71L or one left-opening pixel 71R is disposed in place of one of the two G pixels included in one filter unit U1. Moreover, in the horizontal direction of the imager 244, either the right-opening pixels 71L or the left-opening pixels 71R are disposed in every two filter units U1. Furthermore, in the vertical direction of the imager 244, the right-opening pixels 71L and the left-opening pixels 71R are alternately disposed in every two filter units U1. Meanwhile, the placement of the right-opening pixels 71L and the left-opening pixels 71R can be changed as appropriate.

The imager 244 that is configured in the manner explained above outputs, to the control device 5, image data containing imaging data, which is made of a plurality of electrical signals generated by the imaging pixels 70, and phase difference data, which is made of a plurality of pairs of right and left picture signals generated by the right-opening pixels 71L and the left-opening pixels 71R.

Returning to the explanation with reference to FIGS. 1 and 2, the explanation about the configuration of the endoscope device 2 is continued.

Under the control of the imaging control unit 65, the reading unit 63 reads the electrical signals from the imaging pixels 70 of the pixel portion 60; reads the picture signals from the phase difference pixels 71; and outputs the read signals as image data to the control device 5. The reading unit 63 is configured using a vertical scanning circuit and a horizontal scanning circuit. Meanwhile, an A/D conversion circuit can also be included in the reading unit 63, so that digital image data can be output to the control device 5.

The endoscope recording unit 64 is used to record a variety of information related to the endoscope device 2. For example, the endoscope recording unit 64 is used to record the following: identification information that enables identification of the endoscope device 2; identification information of the imager 244; and reference information indicating the measurement result of the measurements taken in advance about each endoscope device 2. Herein, the reference information indicates the correspondence relationship among the following: the distance between the subject and the imager 244; the information indicating the focal position of the optical system 243; and the ranging information correlated to the distance from the subject. Regarding the details of the reference information, the explanation is given later. In this way, the endoscope recording unit 64 is used to record individual data that is formed by combining the data of the optical system 243 (lens) and the data of the imager 244 as obtained during the manufacturing process and that contains the manufacturing variability. When the endoscope device 2 is connected to the control device 5 (explained later); under the control of a processing control unit 54, the reference information is loaded and recorded in a reference information recording unit 532 of a recording unit 53 of the control device 5 (explained later). Meanwhile, the endoscope recording unit 64 is configured using a nonvolatile memory.

The imaging control unit 65 controls the operations of the imager 244 based on an instruction signal or a control signal input from the control device 5. More particularly, based on a clock signal input from the control device 5, the imaging control unit 65 controls the frame rate and the photographing timing of the imager 244. Herein, the imaging control unit 65 is configured using a timing generator.

The operating unit 22 includes the following: a bending knob 221 that makes the curved portion 25 bend in the vertical direction and the horizontal direction; a treatment tool insertion portion 222 through which a treatment tool such as a laser scalpel or an inspection probe is inserted; and a plurality of switches 223 that receives input of an operation instruction signal regarding the peripheral devices including not only the light source device 3 and the control device 5 but also an insufflation unit, a water supply unit, and a gas supply unit; or receives input of a pre-freeze signal as an instruction for the imager 244 to perform still image photographing; or receives input of a ranging signal as an instruction for measuring the distance from the front end portion 24 of the endoscope device 2 to the subject. The treatment tool inserted from the treatment tool insertion portion 222 passes through a treatment tool channel (not illustrated) in the front end portion 24 and comes out from an opening (not illustrated) of the front end portion 24.

The universal cord 23 includes at least the light guide 241 and a cable assembly, which has one of more cables bundled therein, built-in. The cable assembly represents signal lines for sending and receiving signals among the endoscope device 2, the light source device, and the control device 5; and includes a signal line for sending and receiving setting data, a signal line for sending and receiving image data, and a signal line for sending and receiving driving clock signals meant for driving the imager 244. The universal cord 23 includes a connector unit 27 that is detachably attachable to the light source device 3. The connector unit 27 has a coil cable 27a extending in a coiled manner, and includes a connector unit 28 that is at the extended end of the coil cable 27a and that is detachably attachable to the control device 5.

Configuration of Light Source Device

Given below is the explanation of a configuration of the light source device 3.

The light source device 3 supplies an illumination light from the front end portion 24 of the endoscope device 2 for the purpose of illuminating the subject. The light source device 3 includes a light source unit 31, a light source driver 32, and an illumination control unit 33.

The light source unit 31 irradiates the subject at least either with the white light, which includes the light having the wavelength bandwidth of the red color, the light having the wavelength bandwidth of the green color, and the light having the wavelength bandwidth of the blue color, or with a special light. The light source unit 31 includes a condenser lens 311, a first light source 312, a second light source 313, a third light source 314, a fourth light source 315, and a fifth light source 316.

The condenser lens 311 is configured using one or more lenses. The condenser lens 311 collects the light emitted from the first light source 312, the second light source 313, the third light source 314, the fourth light source 315, and the fifth light source 316; and sends the collected light to the light guide 241.

The first light source 312 is configured using a red LED lamp (LED stands for Light Emitting Diode). Based on the electric current supplied from the light source driver 32, the first light source 312 emits the light having the wavelength bandwidth of the red color (between 610 nm and 750 nm) (hereinafter, simply referred to as "R light").

The second light source 313 is configured using a green LED lamp. Based on the electric current supplied from the light source driver 32, the second light source 313 emits the light having the wavelength bandwidth of the green color (between 500 nm and 560 nm) (hereinafter, simply referred to as "G light").

The third light source 314 is configured using a blue LED lamp. Based on the electric current supplied from the light source driver 32, the third light source 314 emits the light having the wavelength bandwidth of the blue color (between 435 nm and 480 nm) (hereinafter, simply referred to as "B light").

The fourth light source 315 is configured using a violet LED lamp. Based on the electric current supplied from the light source driver 32, the fourth light source 315 emits the light having the wavelength bandwidth of the violet color (between 400 nm and 435 nm) (hereinafter, simply referred to as "V light").

The fifth light source 316 is configured using an umber LED lamp. Based on the electric current supplied from the light source driver 32, the fifth light source 316 emits the light having the wavelength bandwidth of the umber color (between 595 nm and 610 nm) (hereinafter, simply referred to as "A light").

Figure 10:
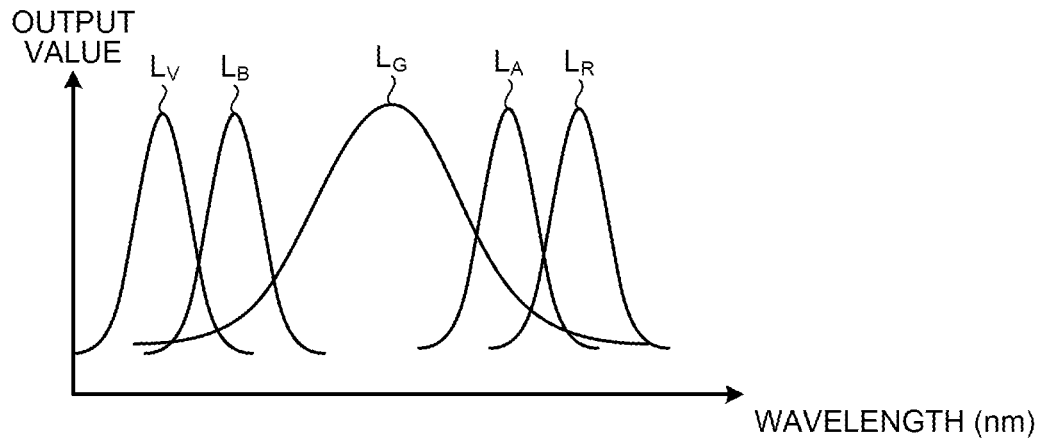
FIG. 10 is a diagram illustrating the spectral characteristics of each type of light emitted by a light source unit.

FIG. 10 is a diagram illustrating the spectral characteristics of each type of light emitted by the light source unit 31. In FIG. 10, the horizontal axis represents the wavelength (nm), and the vertical axis represents the output value. Moreover, in FIG. 10, a curved line L represents the wavelength bandwidth of the violet color; a curved line $L_B$ represents the wavelength bandwidth of the blue color; a curved line $L_G$ represents the wavelength bandwidth of the green color; a curved line $L_A$ represents the wavelength bandwidth of the umber color; and a curved line $L_R$ represents the wavelength bandwidth of the red color.

As illustrated in FIG. 10, the light source unit 31 combines the R light, the G light, the B light, the V light, and the A light; and either emits the white light (R light+G light+B light) or emits a special light (V light+G light or G light+A light).

Returning to the explanation with reference to FIG. 2, the explanation about the configuration of the light source device 3 is continued.

Under the control of the illumination control unit 33, the light source driver 32 supplies an electric current to the first light source 312, the second light source 313, the third light source 314, the fourth light source 315, and the fifth light source 316; and ensures that the light corresponding to the observation mode set in the endoscope system 1 is supplied. More particularly, under the control of the illumination control unit 33, when a normal observation mode is set as the observation mode in the endoscope system 1, the light source driver 32 causes the first light source 312, the second light source 313, and the third light source 314 emit light, so that the white light (hereinafter, simply referred to as "W light") is output. Alternatively, under the control of the illumination control unit 33, when a special light observation mode is set as the observation mode in the endoscope system 1, the light source driver 32 causes the second light source 313 and the fourth light source 315 emit light, so that a special light (hereinafter, simply referred to as "S light") is output.

The illumination control unit 33 controls the lighting-up timing of the light source device 3 based on an instruction signal received from the control device 5. More particularly, the illumination control unit 33 causes the first light source 312, the second light source 313, and the third light source 314 emit light at predetermined periodicity. The illumination control unit 33 is configured using a central processing unit (CPU). Moreover, when the normal observation mode is set as the observation mode in the endoscope system 1, the illumination control unit 33 controls the light source driver 32 and causes the first light source 312, the second light source 313, and the third light source 314 emit light, so that the W light is output. When the special light observation mode is set as the observation mode in the endoscope system 1, the illumination control unit 33 controls the light source driver 32 and combines the second light source 313 and the fourth light source 315, so that the S light is output. Thus, according to the observation mode set in the endoscope system 1, the illumination control unit 33 can control the light source driver 32 in such a way that two or more light sources from among the first light source 312, the second light source 313, the third light source 314, the fourth light source 315, and the fifth light source 316 are combined, and the corresponding light is output.

Configuration of Display Device

Given below is the explanation of a configuration of the display device 4.

The display device 4 displays a display image based on the image data that is generated by the endoscope device 2 and that is received from the control device 5. Moreover, the display device 4 displays a variety of information related to the endoscope system 1. The display device 4 is configured using a liquid crystal display panel or an organic electroluminescence (organic EL) display panel.

Configuration of Control Device

Given below is the explanation of a configuration of the control device 5.

The control device 5 receives image data generated by the endoscope device 2, performs predetermined image processing with respect to the received image data, and outputs the processed image data to the display device 4. Moreover, the control device 5 comprehensively controls the overall operations of the endoscope system 1. The control device 5 includes an image processing unit 51, an input unit 52, the recording unit 53, and the processing control unit 54.

Under the control of the processing control unit 54, the image processing unit 51 receives the image data generated by the endoscope device 2, performs predetermined image processing with respect to the received image data, and outputs the processed image data to the display device 4. The image processing unit 51 is configured using a memory and a processor that includes hardware such as a graphics processing unit (GPU), a digital signal processing (DSP), or a field programmable gate array (FPGA).

The input unit 52 receives input of an instruction signal as an instruction for performing operations of the endoscope system 1, or receives input of a ranging signal as an instruction for measuring the distance from the front end portion 24 of the endoscope device 2 to the subject; and outputs the instruction signal or the ranging signal to the processing control unit 54. For example, the input unit 52 receives input of a ranging signal as an instruction for distance measurement, and outputs the ranging signal to the processing control unit 54. The input unit 52 is configured using switches, buttons, and a touch-sensitive panel.

The recording unit 53 is used to record various computer programs executed in the endoscope system 1, and to record the data being used in the endoscope system 1 and the image data generated by the endoscope device 2. The recording unit 53 is configured using a volatile memory, a nonvolatile memory, or a memory card. The recording unit 53 includes a program recording unit 531 used to store various computer programs executed in the endoscope system 1, and includes the reference information recording unit 532.

The reference information recording unit 532 records, for each endoscope device 2, a plurality of sets of reference information that indicates the correspondence relationship among the following: the distance between the subject and the imager 244; the information indicating the focal position of the optical system 243; and the ranging information correlated to the distance from the subject. The sets of reference information are recorded in the reference information recording unit 532 in a corresponding manner to the identification information of the concerned endoscope device 2. Regarding the sets of reference information recorded in the reference information recording unit 532, when the endoscope device 2 is connected to the control device 5, the processing control unit 54 (explained later) obtains the identification information of the endoscope device 2 from the endoscope recording unit 64 of the endoscope device 2; obtains the reference information associated to the obtained identification information; and records (stores) the identification information and the reference information in a corresponding manner. Alternatively, regarding the sets of reference information recorded in the reference information recording unit 532, when the endoscope device 2 is connected to the control device 5, the processing control unit 54 (explained later) can obtain the identification information of the endoscope device 2 from the endoscope recording unit 64 of the endoscope device 2; and can obtain the reference information corresponding to the obtained identification information from a server (not illustrated) via a network and record the reference information.

Figure 11:
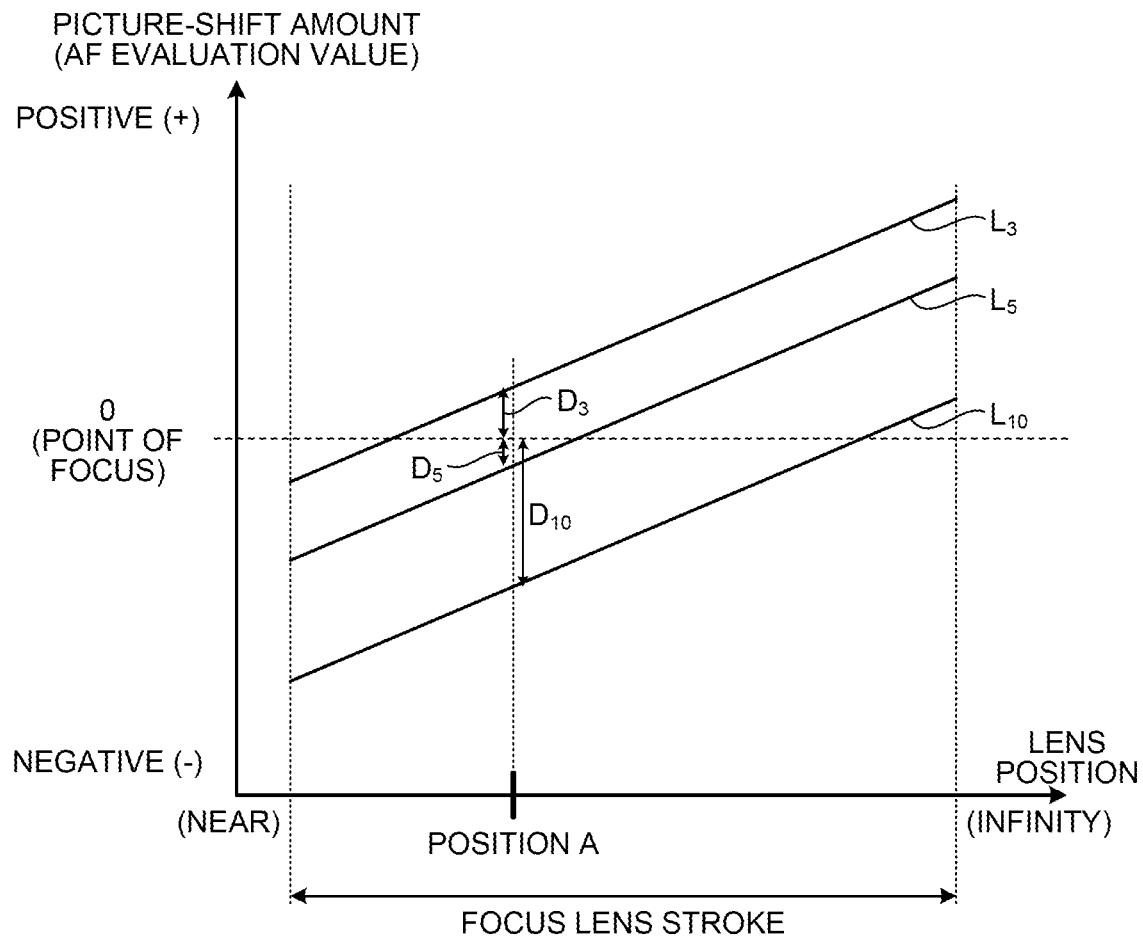
FIG. 11 is a diagram illustrating an example of reference information recorded in a reference information recording unit.

FIG. 11 is a diagram illustrating an example of the reference information recorded in the reference information recording unit 532. In FIG. 11, the horizontal axis represents the lens position of the focus lens 243a of the optical system 243, and the vertical axis represents the picture-shift amount (the AF evaluation value). Moreover, in FIG. 11, a straight line $L_3$ indicates that the subject distance between the imager 244 and the subject is 3 mm and indicates the picture-shift characteristics between the picture-shift amount, which indicates the ranging information correlated to the distance from the subject, and the focal position of the optical system 243. Furthermore, a straight line $L_5$ indicates that the subject distance between the imager 244 and the subject is 5 mm and indicates the picture-shift characteristics between the picture-shift amount, which indicates the ranging information correlated to the distance from the subject, and the focal position of the optical system 243. Moreover, a straight line $L_{10}$ indicates that the subject distance between the imager 244 and the subject is 10 mm and indicates the picture-shift characteristics between the picture-shift amount, which indicates the ranging information correlated to the distance from the subject, and the focal position of the optical system 243.

As indicated by the straight lines $L_3$, $L_5$, and $L_{10}$ illustrated in FIG. 11, in the reference information recording unit 532, the reference information is recorded that indicates the correspondence relationship among the following: the subject distance between the imager 244 and the subject; the information indicating the focal position of the optical system 243; and the picture-shift amount (the AF evaluation value) indicating the ranging information correlated to the distance from the subject. For example, as illustrated in FIG. 11, in the reference information, when the focus lens 243a of the optical system 243 is stationary at a focus point A, if the picture-shift amount from the focus position (0) is equal to D10, then the subject distance can be determined to be equal to 10 mm. In an identical manner, in the reference information, when the focus lens 243a of the optical system 243 is stopped at the focus point A, if the picture-shift amount from the focus position (0) is equal to D5, then the subject distance can be determined to be equal to 5 mm; and, if the picture-shift amount from the focus position (0) is equal to D3, then the subject distance can be determined to be equal to 3 mm. Meanwhile, in FIG. 11, for the ease of explanation, only three subject distances are cited. In the reference information, for each subject distance, the focal position of the optical system 243 is recorded in a corresponding manner to the picture-shift amount (the AF evaluation value) indicating the ranging information correlated to the distance from the subject.

The processing control unit 54 includes a memory and a processor that is configured using at least one hardware component such as an FPGA or a CPU. The processing control unit 54 controls the constituent elements of the endoscope system 1. The processing control unit 54 includes an obtaining unit 541, an arithmetic processing unit 542, a determining unit 543, a driving control unit 544, and a display control unit 545.

The obtaining unit 541 obtains, from the endoscope device 2, the image data (image signals and picture signals) generated by the imager 244 at each of a plurality of mutually different focal positions. More particularly, the obtaining unit 541 obtains the image data (image signals and picture signals) generated by the imager 244 when the optical system 243 becomes stationary at a plurality of mutually different focal positions. For example, from the imager 244, the obtaining unit 541 obtains a first picture signal generated by the phase difference pixels 71 in the state in which the optical system 243 has a first focal position, and obtains a second picture signal generated by the phase difference pixels 71 in the state in which the optical system 243 has a second focal position. The first focal position represents the focal position of the optical system 243 at the point of time at which a ranging signal is input. The second focal position represents the focal position of the optical system 243 at the point of time at which the optical system 243 moves away from its focal position attained at the point of time at which the ranging signal was input.

The arithmetic processing unit 542 performs arithmetic processing with respect to first ranging information based on the first picture signal obtained by the obtaining unit 541, and performs arithmetic processing with respect to second ranging information based on the second picture signal obtained by the obtaining unit 541. As arithmetic processing, based on the first ranging information, based on the information indicating the first focal position of the optical system, and based on the reference information recorded in the reference information recording unit 532; the arithmetic processing unit 542 estimates a first subject distance corresponding to the first ranging information. Furthermore, based on the estimated first subject distance, based on the second focal position of the optical system 243, and based on the reference information recorded in the reference information recording unit 532; the arithmetic processing unit 542 estimates the ranging information corresponding to the second focal position. More particularly, the arithmetic processing unit 542 performs arithmetic processing with respect to a plurality of sets of ranging information corresponding to each of a plurality of focal positions. For example, based on the picture signals (the phase difference signals) included in the image data, the arithmetic processing unit 542 performs arithmetic processing with respect to the ranging information indicating the distance to the subject from the front end portion 24 of the endoscope device 2 or from the imager 244. Then, the arithmetic processing unit 542 calculates, as the variation, the difference or the inclination between the calculation results of the first ranging information, which is calculated based on the first picture signal at the focal position of the optical system 243 at the point of time at which the ranging signal is input, and the second ranging information, which is calculated based on the second picture signal obtained when the focal position of the optical system 243 changes from the focal position attained at the point of time at which the ranging signal was input.

The determining unit 543 performs arithmetic processing based on: the reference information that indicates the correspondence relationship among the distance between the subject and the imager 244, the information indicating the focal position of the optical system 243, and the ranging information (the picture-shift amount) correlated to the distance from the subject as recorded in the reference information recording unit 532; and the first ranging information and the second ranging information calculated by the arithmetic processing unit 542. Then, the determining unit 543 outputs the arithmetic processing result. As the arithmetic processing, based on the reference information recorded in the reference information recording unit 532, the first ranging information calculated by the arithmetic processing unit 542, and the second ranging information calculated by the arithmetic processing unit 542; the determining unit 543 determines the degree of reliability of the first ranging information. More particularly, as the arithmetic processing, based on the ranging information corresponding to the second focal position of the optical system 243 and based on the second ranging information calculated by the arithmetic processing unit 542, the determining unit 543 determines the degree of reliability of the first ranging information. For example, based on the reference information recorded in the reference information recording unit 532 and based on the ranging calculation result obtained by the arithmetic processing unit 542, the determining unit 543 determines the degree of reliability of one or more of a plurality of sets of ranging information. More particularly, immediately after a ranging signal that serves as an instruction for distance measurement is input from the operating unit 22 or the input unit 52, the determining unit 543 determines the degree of reliability of the ranging information (the first ranging information) calculated by the arithmetic processing unit 542. Moreover, with respect to each of a plurality of sets of image data obtained by the obtaining unit 541, the determining unit 543 determines whether or not the motion vector is equal to or greater than a threshold value. More particularly, the determining unit 543 calculates the motion vector from the picture signals obtained by the obtaining unit 541, and determines whether or not the motion vector is equal to or greater than a threshold value.

Based on the ranging information calculated by the arithmetic processing unit 542, the driving control unit 544 drives the driving unit 245 so as to move the optical system 243 along the light axis L1, and adjusts the focal position of the optical system 243.

The display control unit 545 controls the image processing unit 51 and controls the display form of the display device 4. More particularly, the display control unit 545 displays, in the display device 4, a display image based on the image data with respect to which the image processing unit 51 has performed image processing.

Operations in Endoscope System

Figure 12:
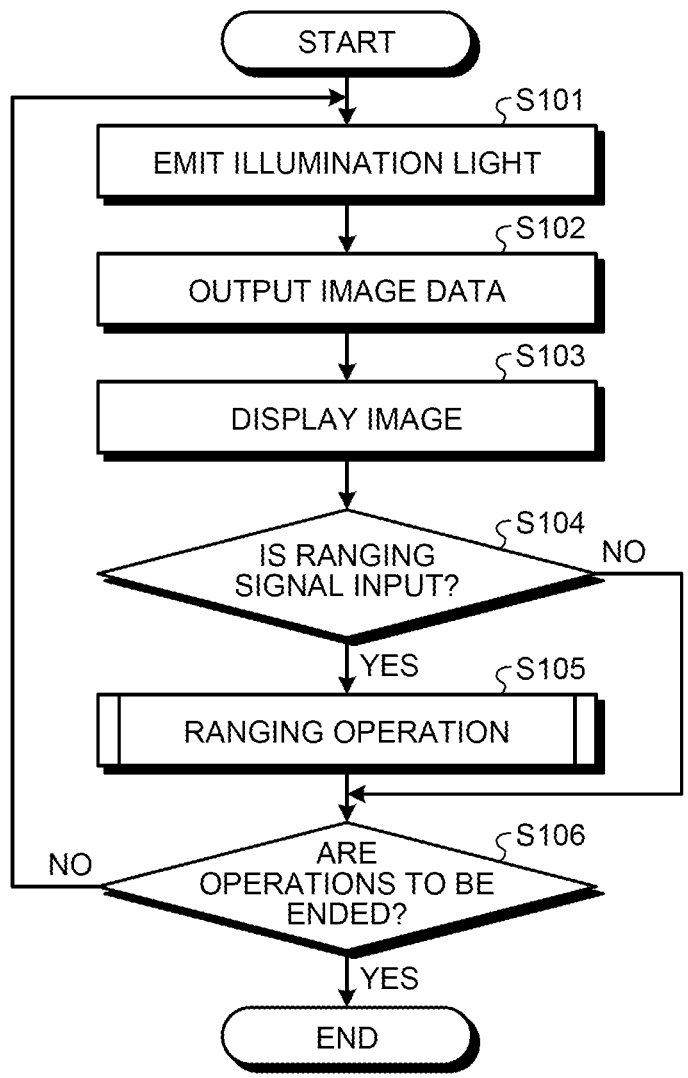
FIG. 12 is a flowchart for explaining the overview of the operations performed in the endoscope system.

Given below is the explanation of the operations performed in the endoscope system 1. FIG. 12 is a flowchart for explaining the overview of the operations performed in the endoscope system 1.

As illustrated in FIG. 12, firstly, the processing control unit 54 causes the light source device 3 emit the illumination light (Step S101). More particularly, the processing control unit 54 controls the illumination control unit 33 to cause the first light source 312, the second light source 313, and the third light source 314 of the light source device 3 emit light. As a result, the W light is output from the front end portion 24 of the endoscope device 2 toward the subject.

Then, the processing control unit 54 outputs, to the control device 5, the image data generated by the imager 244 as a result of receiving (getting exposed to) the reflected light coming from the subject (Step S102).

Subsequently, the processing control unit 54 displays, in the display device 4, a display image based on the display image data obtained as a result of predetermined image processing performed by the image processing unit 51 with respect to the image data input from the imager 244 (Step S103).

Then, if a ranging signal serving as an instruction for measuring the distance from the front end portion 24 of the endoscope device 2 to the subject is input from the operating unit 22 or the input unit 52 (Yes at Step S104), the endoscope system 1 performs a ranging operation for measuring the distance from the front end portion 24 of the endoscope device 2 to the subject (Step S105). Regarding the ranging operation, the detailed explanation is given later. After the operation at Step S105 is performed, the system control proceeds to Step S106 (explained later).

On the other hand, at Step S104, if a ranging signal serving as an instruction for measuring the distance from the front end portion 24 of the endoscope device 2 to the subject is not input from the operating unit 22 or the input unit 52 (No at Step S104), then the system control proceeds to Step S106 (explained below).

Subsequently, when an end signal serving as an instruction for ending the examination of the subject is input from the operating unit 22 or the input unit 52 (Yes at Step S106), the endoscope system 1 ends the operations. On the other hand, if an end signal serving as an instruction for ending the examination of the subject is not input from the operating unit 22 or the input unit 52 (No at Step S106), then the system control returns to Step S101.

Ranging Operation

Figure 13:
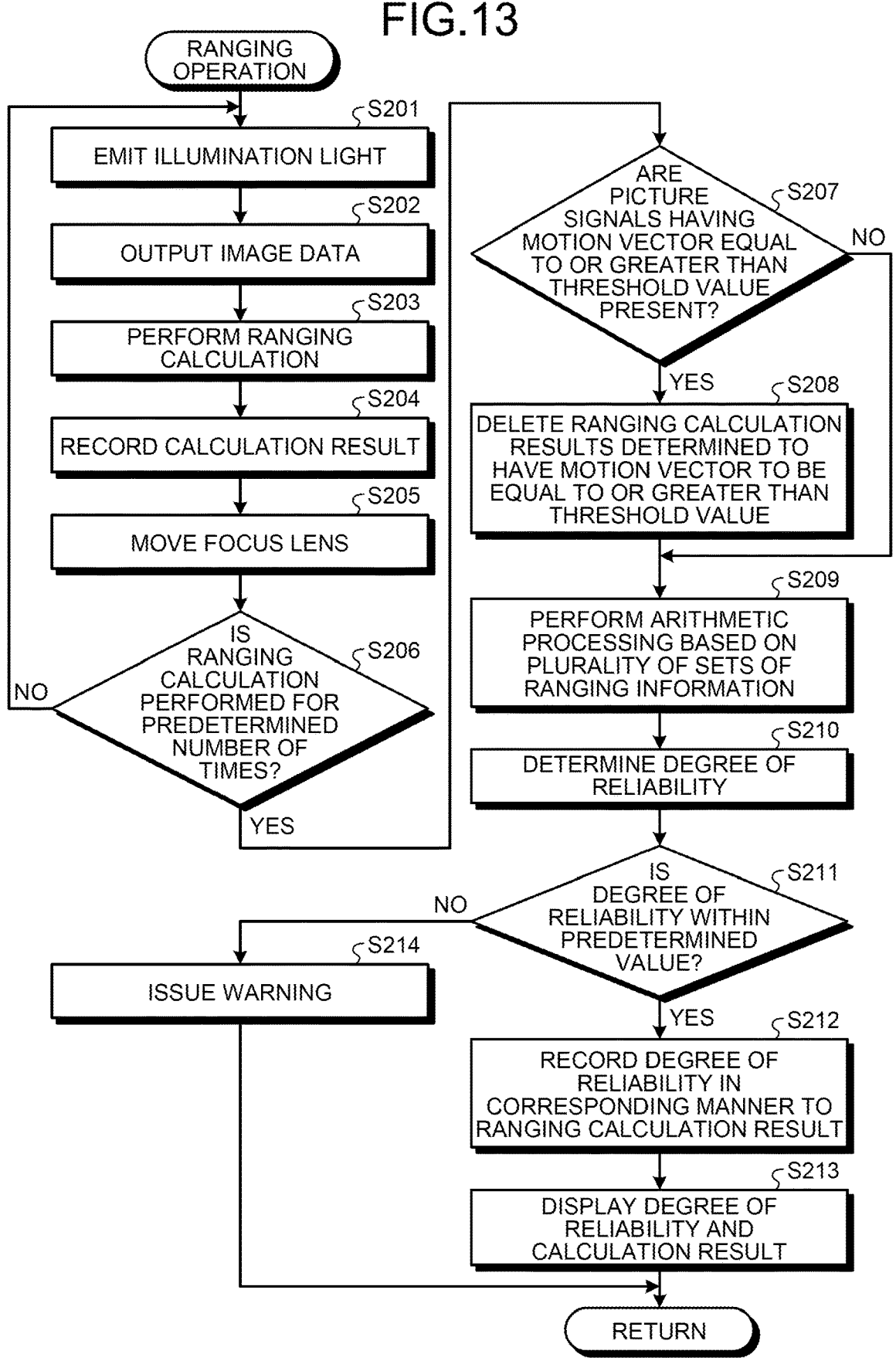
FIG. 13 is a flowchart for explaining the overview of a ranging operation.
Figure 14:
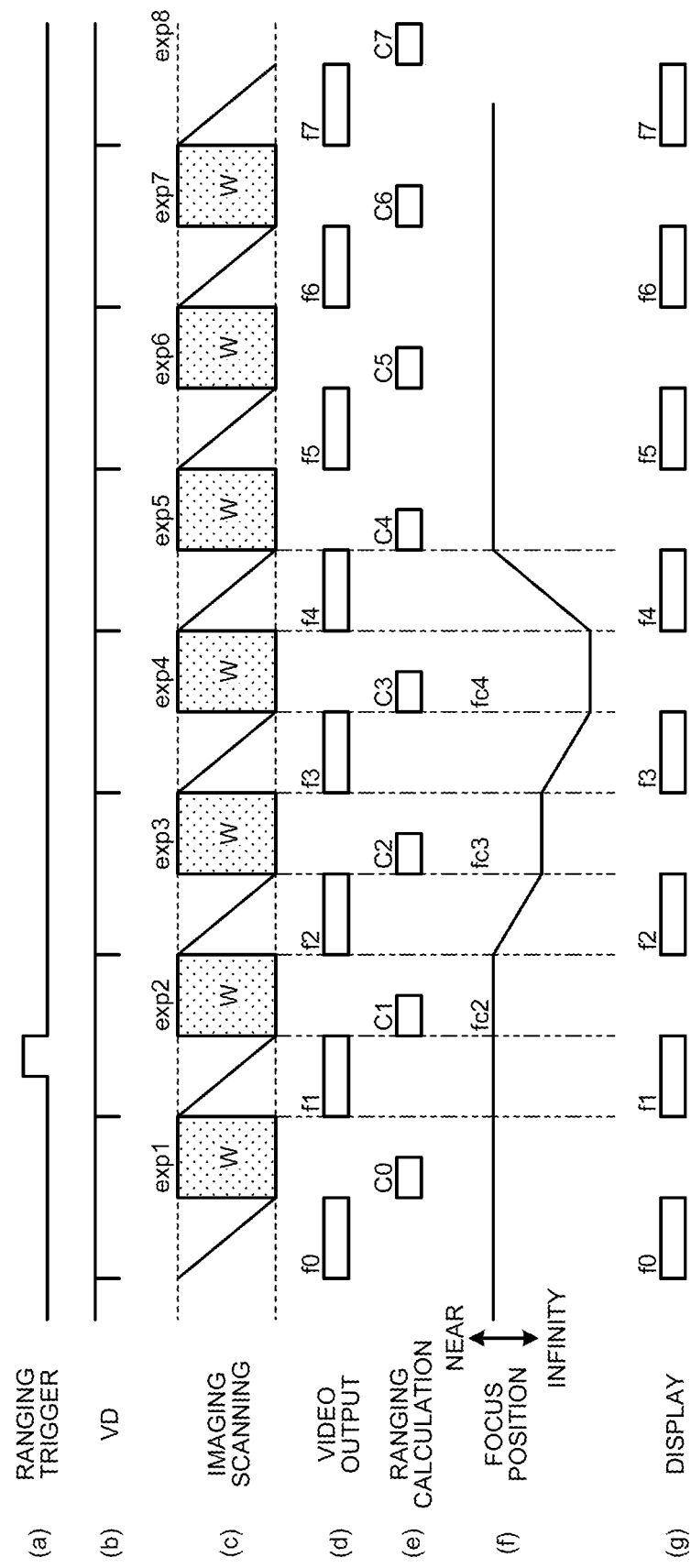
FIG. 14 is a timing chart corresponding to the ranging operation.

Given below is the detailed explanation of the ranging operation performed at Step S105 illustrated in FIG. 12. FIG. 13 is a flowchart for explaining the overview of the ranging operation. FIG. 14 is a timing chart corresponding to the ranging operation. In FIG. 14, starting from the top, (a) represents the rising timing of a ranging trigger in the ranging signal; (b) represents the vertical synchronization timing; (c) represents the imaging scanning (exposure period) of the imager 244; (d) represents the video output timing at which the image data is output from the imager 244; (e) represents the ranging calculation timing; (f) represents the focal position of the optical system 243; and (g) represents the display timing.

As illustrated in FIG. 13, firstly, the driving control unit 544 causes the light source device 3 emit the illumination light (Step S201); and outputs, to the control device 5, the image data generated by the imager 244 as a result of receiving (getting exposed to) the reflected light coming from the subject (Step S202). More particularly, as illustrated in FIG. 14, firstly, at the point of time of rising of the ranging trigger due to the input of a ranging signal from the operating unit 22 or the input unit 52, the display control unit 545 maintains the display of a display image f1 so that the display image f1 remains displayed in the display device 4. Then, in the state in which the optical system 243 is stationary at a focal position fc2, the driving control unit 544 causes the imager 244 receive (for an exposure period exp2) the reflected light coming from the subject, and then causes the imager 244 output an imaging image f2 that is based on the image data.

Then, based on the pairs of right and left picture signals of the phase difference pixels 71 that are included in the imaging image f2 input from the imager 244, the arithmetic processing unit 542 performs ranging calculation for calculating the distance from the front end portion 24 of the endoscope device 2 or from the imager 244 to the subject (Step S203), and records the calculation result in the recording unit 53 (Step S204). More particularly, as illustrated in FIG. 14, based on the pairs of right and left picture signals of the phase difference pixels 71 included in the imaging image f2 that is based on the image data input from the imager 244, the arithmetic processing unit 542 performs ranging calculation for calculating the distance from the front end portion 24 of the endoscope device 2 or from the imager 244 to the subject, and records a calculation result c2 in the recording unit 53.

Subsequently, based on the calculation result c2 obtained by the arithmetic processing unit 542, the driving control unit 544 drives the driving unit 245 and moves the focus lens 243a along the light axis L1 (Step S205). In that case, as illustrated in FIG. 14, the driving control unit 544 moves the focus lens 243a along the light axis L1 during a reading period in which the image data is read from the imager 244. As a result, it becomes possible to prevent the occurrence of an error in the ranging information attributed to the picture changes occurring during the movement period in which the optical system 243 moves during the exposure period.

FIG. 15 is a diagram that schematically illustrates the ranging region in the imager 244. FIG. 16 is a diagram that schematically illustrates the focal position direction at each ranging point. FIG. 17 is a diagram that schematically illustrates the movement direction and the movement amount of the focus lens 243a. In FIGS. 15 and 16 is illustrated an example in which the imager 244 is divided into 5×5 ranging regions (a1 to a25). Moreover, in FIG. 16, "N" represents the near-side direction in the ranging region, and "F" represents the far-side direction in the ranging region.

As illustrated in FIGS. 15 to 17, when the focus lens 243a is on the near side and when the number of near-side directions in the focal position directions of the ranging regions (i.e., the count of 19) is greater than the number of far-side directions (i.e., the count of 6) (i.e., when N>F holds true), the driving control unit 544 drives the driving unit 245 and moves the focus lens 243a along the light axis L1 in the far-side direction. For example, as illustrated in FIG. 17, the driving control unit 544 drives the driving unit 245 to move the focus lens 243a along the light axis L1 to a focal position fc3.

Returning to the explanation with reference to FIG. 13, the operations performed from Step S206 onward are explained below.

At Step S206, the processing control unit 54 determines whether or not the ranging calculation has been performed for a predetermined number of times such as thrice. If it is determined that the ranging calculation has been performed for a predetermined number of times (Yes at Step S206), then the system control proceeds to Step S207 (explained later).

On the other hand, if it is determined that the ranging calculation has not been performed for a predetermined number of times (No at Step S206), then the system control returns to Step S201. In that case, as illustrated in FIG. 14, in the ranging calculation performed for the second time, in the state in which the optical system 243 is stationary at the focal position fc3, the driving control unit 544 causes the imager 244 receive (for an exposure period exp3) the reflected light coming from the subject, and causes the imager 244 output an imaging image f3 that is based on the image data. Then, based on the pairs of right and left picture signals of the phase difference pixels 71 included in the imaging image f3 that is input from the imager 244, the arithmetic processing unit 542 performs ranging calculation and records a calculation result c3 in the recording unit 53. Subsequently, the processing control unit 54 drives the driving unit 245 and moves the focus lens 243a along the light axis L1 to a focal position fc4.

Moreover, as illustrated in FIG. 14, in the ranging calculation performed for the third time, in the state in which the optical system 243 is stationary at the focal position fc4, the processing control unit 54 causes the imager 244 receive (for an exposure period exp4) the reflected light coming from the subject, and causes the imager 244 output the imaging image f4 that is based on the image data. Then, based on the pairs of right and left picture signals of the phase difference pixels 71 included in the imaging image f4 that is input from the imager 244, the arithmetic processing unit 542 performs ranging calculation and records a calculation result c4 in the recording unit 53. Subsequently, the driving control unit 544 drives the driving unit 245, and moves the focus lens 243a along the light axis L1 back to the focal position fc2 that was the focal position before starting the ranging operation. Meanwhile, with reference to FIG. 14, although the ranging calculation is performed thrice, the number of times of performing the ranging calculation can be changed as appropriate. For example, in a nonilluminated environment, or in a low illumination environment, or according to the observation position for the endoscope device 2, the number of times of performing the ranging calculation can be changed.

Returning to the explanation with reference to FIG. 13, the operations performed from Step S207 onward are explained below.

At Step S207, the determining unit 543 determines whether or not a plurality of picture signals generated by the imager 244 during the ranging calculation includes picture signals having the motion vector equal to or greater than a threshold value. When the determining unit 543 determines that the picture signals include picture signals having the motion vector equal to or greater than the threshold value (Yes at Step S207), the system control proceeds to Step S208 (explained below). On the other hand, if the determining unit 543 determines that the picture signals do not include picture signals having the motion vector equal to or greater than the threshold value (No at Step S207), then the system control proceeds to Step S209 (explained later).

At Step S208, the arithmetic processing unit 542 deletes, from the recording unit 53, the ranging calculation results that are based on the imaging images regarding which the determining unit 543 determines that the motion vector is equal to or greater than the threshold value.

Then, the arithmetic processing unit 542 performs arithmetic processing based on the reference information recorded in the reference information recording unit 532 and based on a plurality of ranging calculation results recorded in the recording unit 53 (for example, the first ranging information and the second ranging information) (Step S209). Based on the reference information recorded in the reference information recording unit 532 and based on the calculation results c2 to c4 recorded in the recording unit 53, the arithmetic processing unit 542 calculates the variation in the ranging information attributed to the changes in the focal position of the optical system 243. For example, as the arithmetic processing, based on the calculation result c2 (the first ranging information), the information indicating the first focal position (the focus position fc3), and the reference information recorded in the reference information recording unit 532; the arithmetic processing unit 542 estimates the first subject distance corresponding to the calculation result c2 (the first ranging information). Moreover, based on the estimated first subject distance, the information indicating the second focal position (the focus position c4), and the reference information; the arithmetic processing unit 542 estimates the ranging information (the picture-shift amount) corresponding to the second focal position.

Then, the determining unit 543 determines the degree of reliability of one of a plurality of focal positions (Step S210). More particularly, the determining unit 543 determines the degree of reliability of the calculation result c2 obtained as a result of performing ranging calculation immediately after the input of a ranging trigger.

Figure 18:
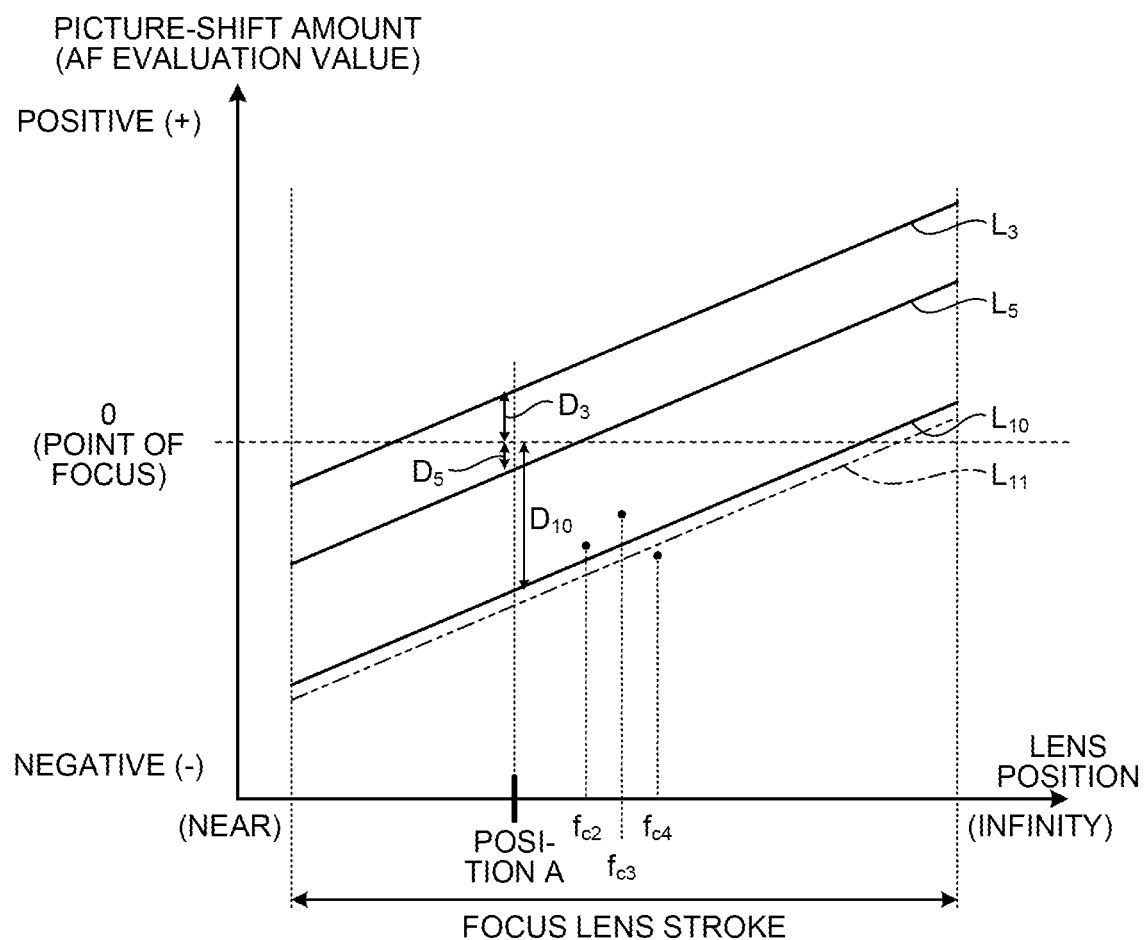
FIG. 18 is a diagram that schematically illustrates the overview of a determination method implemented by a determining unit.

FIG. 18 is a diagram that schematically illustrates the overview of the determination method implemented by the determining unit 543. In FIG. 18, the horizontal axis represents the lens position of the focus lens 243a, and the vertical axis represents the AF evaluation value (the picture-shift amount). Moreover, in FIG. 18, a straight line $L_{11}$ indicates the picture-shift characteristics based on the variation calculated by the arithmetic processing unit 542.

As illustrated in FIG. 18, firstly, the determining unit 543 determines the degree of coincidence of the straight line $L_{11}$, which indicates the ranging calculation result attributed to the changes in the focal position of the optical system 243 based on the calculation results c2 to c4 obtained by the arithmetic processing unit 542, with each of the straight lines $L_3$, $L_5$, and $L_{10}$; and determines the picture-shift characteristics having the highest degree of coincidence. In the case illustrated in FIG. 18, the determining unit 543 determines that the straight lines $L_{11}$ and $L_{10}$ have the highest degree of coincidence. Then, the determining unit 543 determines (calculates) the degree of coincidence between the straight lines $L_{11}$ and $L_{10}$ as the degree of reliability, as well as determines the subject distance to be equal to 10 mm.

Returning to the explanation with reference to FIG. 13, the operations performed from Step S211 onward are explained below.

At Step S211, the determining unit 543 determines whether or not the degree of reliability is within a predetermined value. If the determining unit 543 determines that the degree of reliability is within a predetermined value (Yes at Step S211), then the system control proceeds to Step S212 (explained below). On the other hand, if the determining unit 543 determines that the degree of reliability is not within a predetermined value (No at Step S211), then the system control proceeds to Step S214 (explained later).

At Step S212, the determining unit 543 records the degree of reliability and the ranging calculation result in a corresponding manner in the recording unit 53.

Then, the display control unit 545 displays, in the display device 4, the degree of reliability determined by the determining unit 543 and the ranging calculation result obtained by the arithmetic processing unit 542 (Step S213). After the operation at Step S213 is performed, the system control returns to the main routine illustrated in FIG. 12.

At Step S214, the display control unit 545 displays, in the display device 4, a warning indicating that the degree of reliability in the ranging calculation result is not normal. For example, the display control unit 545 issues a warning by displaying the ranging calculation result in red color in the display device 4 or by making the display device 4 output a buzzer sound. After the operation at Step S214 is performed, the system control returns to the main routine illustrated in FIG. 12.

According to the first embodiment described above, based on the reference information recorded in the reference information recording unit 532 and based on the first ranging information and the second ranging information calculated by the arithmetic processing unit 542, the determining unit 543 performs arithmetic processing and outputs the calculation result. That enables achieving enhancement in the accuracy of the ranging calculation.

Moreover, according to the first embodiment, based on the picture signals generated by a plurality of phase difference pixels 71, the driving control unit 544 drives the driving unit 245 of the endoscope device 2 so as to move the focus lens 243a of the optical system 243 along the light axis L1, and thus changes the focal position of the optical system 243. As a result, the arithmetic processing unit 542 becomes able to calculate the variation attributed to the changes in a plurality of mutually different focal positions.

Furthermore, according to the first embodiment, immediately after the input of a ranging signal from the input unit 52 or the operating unit 22, the determining unit 543 determines the degree of reliability of the ranging information calculated by the arithmetic processing unit 542. Hence, it becomes possible to obtain the degree of reliability of the ranging information at the user-desired timing.

Moreover, according to the first embodiment, the arithmetic processing unit 542 performs arithmetic processing by excluding the ranging information of the image data regarding which the determining unit 543 determines that the motion vector is equal to or greater than a threshold value. That enables exclusion of the ranging information having a large amount of movement of the endoscope device 2, thereby enabling achieving enhancement in the degree of reliability of the ranging information.

Second Embodiment

Given below is the explanation of a second embodiment. In the first embodiment described above, when a ranging signal is input, the focus lens 243a is moved along the light axis L1 and the focal position of the optical system 243 is changed. In contrast, in the second embodiment, when a ranging signal is input, the wavelength bandwidth of the illumination light emitted by the light source device is changed so as to generate a parallax component with respect to the phase difference pixels, and accordingly the focal position of the optical system is changed from the first focal position to the second focal position. In the following explanation, a configuration of the endoscope system according to the second embodiment is explained, and that is followed by the explanation of the ranging operation performed in the endoscope system according to the second embodiment. Meanwhile, the configuration identical to the endoscope system 1 according to the first embodiment is referred to by the same reference numerals, and the detailed explanation is not given again.

Configuration of Endoscope System

Figure 19:
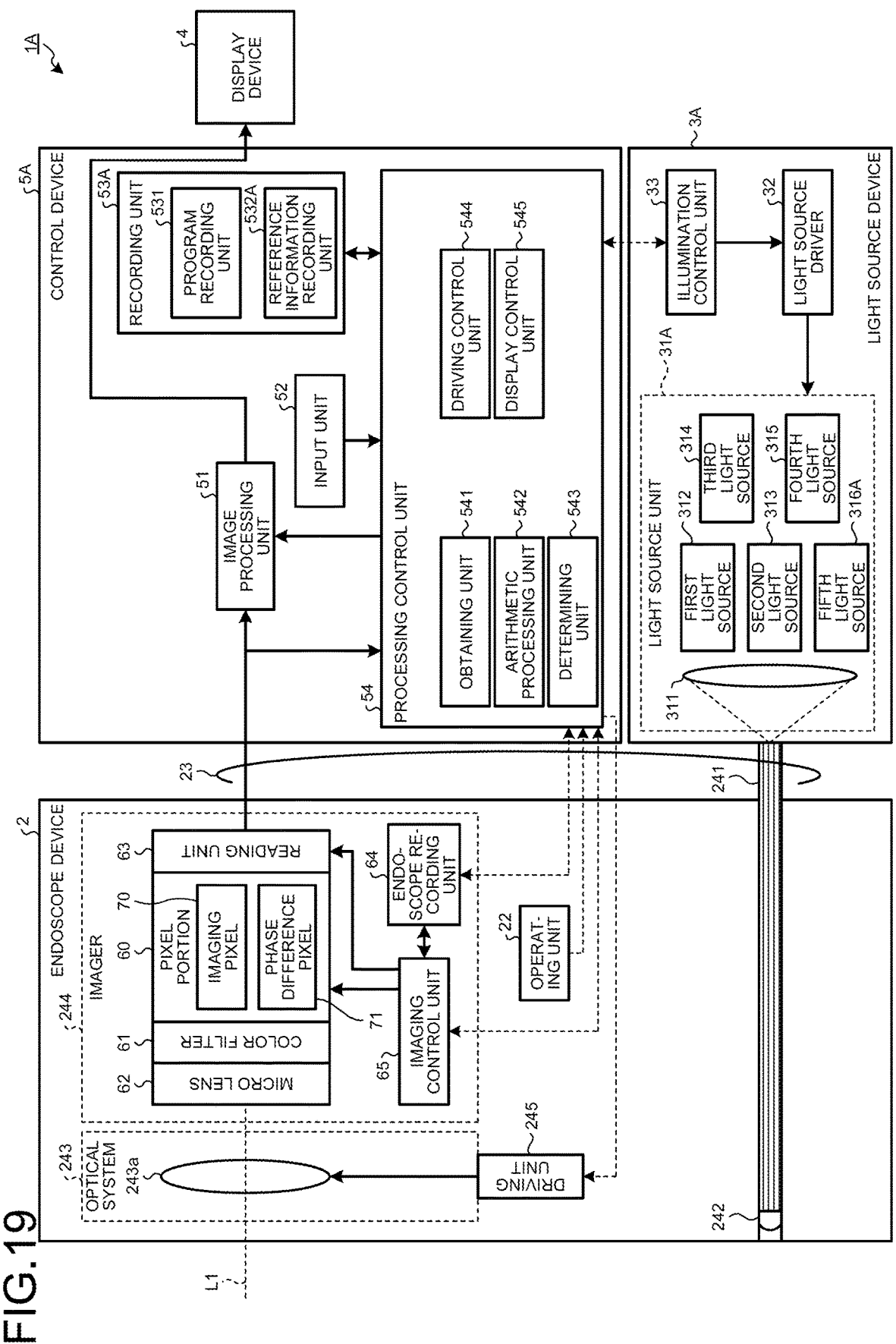
FIG. 19 is a block diagram illustrating a functional configuration of the main parts of an endoscope system according to a second embodiment.

FIG. 19 is a block diagram illustrating a functional configuration of the main parts of the endoscope system according to the second embodiment. An endoscope system 1A illustrated in FIG. 19 includes a light source device 3A and a control device 5A in place of the light source device 3 and the control device 5, respectively, according to the first embodiment.

The light source device 3A includes a light source unit 31A in place of the light source unit 31 according to the first embodiment. Moreover, the light source unit 31A includes a fifth light source 316A in place of the fifth light source 316. The fifth light source 316A is made of an infrared LED lamp that, based on the electric current supplied from the light source driver 32, emits light having the infrared wavelength bandwidth (for example, between 780 nm to 1000 nm) (hereinafter, simply referred to as "IR light").

The control device 5A includes a recording unit 53A in place of the recording unit 53 according to the first embodiment. The recording unit 53A is used to record various computer programs executed in the endoscope system 1A, and to record the data being used in the endoscope system 1A and the image data generated by the endoscope device 2. The recording unit 53A is configured using a volatile memory, a nonvolatile memory, or a memory card. The recording unit 53 includes the program recording unit 531 and a reference information recording unit 532A.

Figure 20:
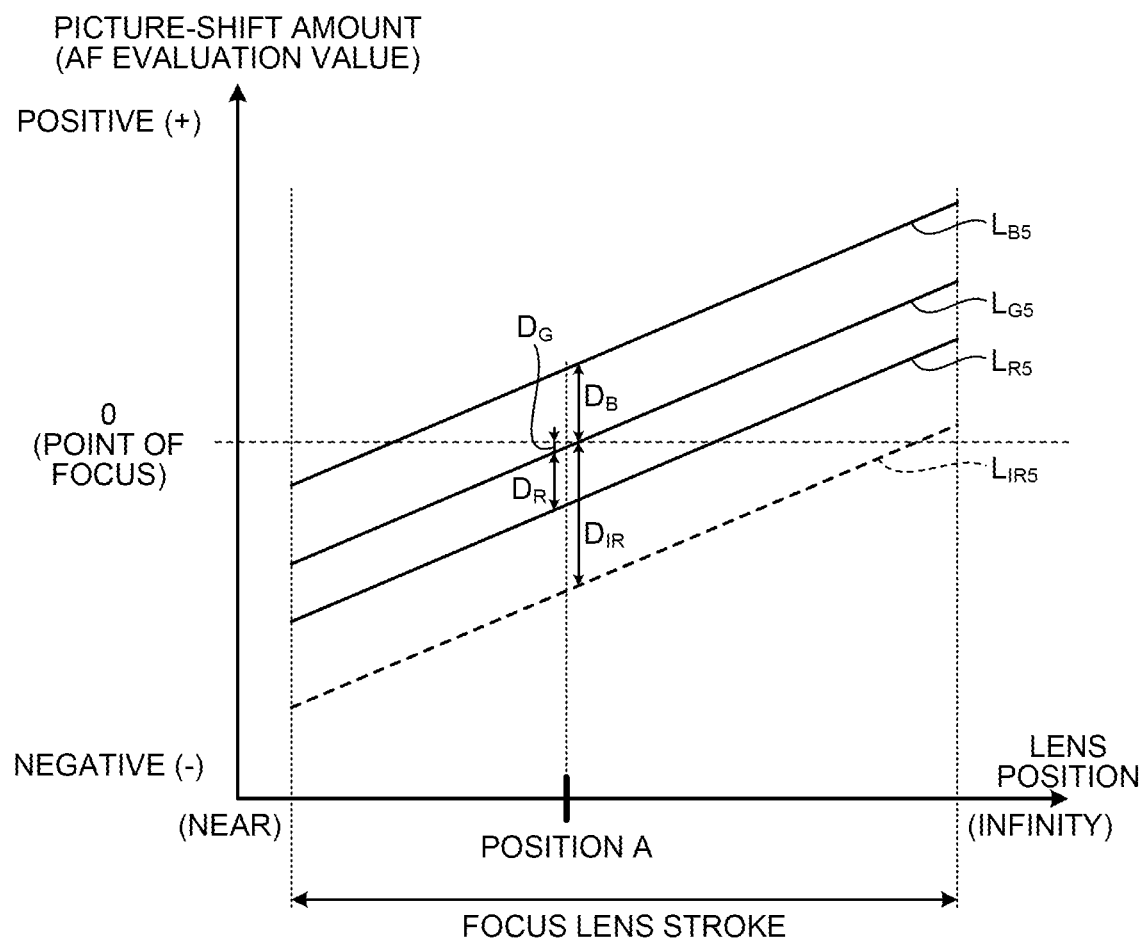
FIG. 20 is a diagram illustrating an example of reference information recorded in a reference information recording unit.

FIG. 20 is a diagram illustrating an example of the reference information recorded in the reference information recording unit 532A. In FIG. 20, the horizontal axis represents the lens position of the focus lens of the optical system 243, and the vertical axis represents the picture-shift amount (the AF evaluation value). Moreover, in FIG. 20, a straight line $L_{B5}$ indicates that the subject distance between the imager 244 and the subject is 5 mm at the time of emission of the light having the wavelength bandwidth of the blue color, and indicates the picture-shift characteristics between the picture-shift amount, which indicates the ranging information correlated to the distance from the subject, and the focal position. Moreover, a straight line $L_{G5}$ indicates that the subject distance between the imager 244 and the subject is 5 mm at the time of emission of the light having the wavelength bandwidth of the green color, and indicates the picture-shift characteristics between the picture-shift amount, which indicates the ranging information correlated to the distance from the subject, and the focal position. Furthermore, a straight line $L_{R5}$ indicates that the subject distance between the imager 244 and the subject is 5 mm at the time of emission of the light having the wavelength bandwidth of the red color, and indicates the picture-shift characteristics between the picture-shift amount, which indicates the ranging information correlated to the distance from the subject, and the focal position. Moreover, a straight line $L_{IR5}$ indicates that the subject distance between the imager 244 and the subject is 5 mm at the time of emission of the light having the wavelength bandwidth of a special light (near-infrared), and indicates the picture-shift characteristics between the picture-shift amount, which indicates the ranging information correlated to the distance from the subject, and the focal position.

As illustrated in the straight lines $L_{B5}$, $L_{G5}$, and $L_{R5}$; for each wavelength bandwidth, the subject distance, the focal position of the optical system 243, and the picture-shift amount indicating the ranging information correlated to the distance from the subject are recorded in a corresponding manner. For example, as illustrated in FIG. 20, in the reference information, when the focus lens 243a of the optical system 243 is stationary at the focus point A and when the R light is emitted from the light source device 3A, if the picture-shift amount from the focus position (0) is equal to $D_R$, the subject distance can be determined to be equal to 5 mm. Meanwhile, with reference to FIG. 20, for the ease of explanation, only one subject distance is cited. However, in the reference information, the picture-shift characteristics between the picture-shift amount of each of a plurality of subject distances and the focal position of the optical system 243 are recorded for each wavelength bandwidth.

Ranging Operation

Figure 21:
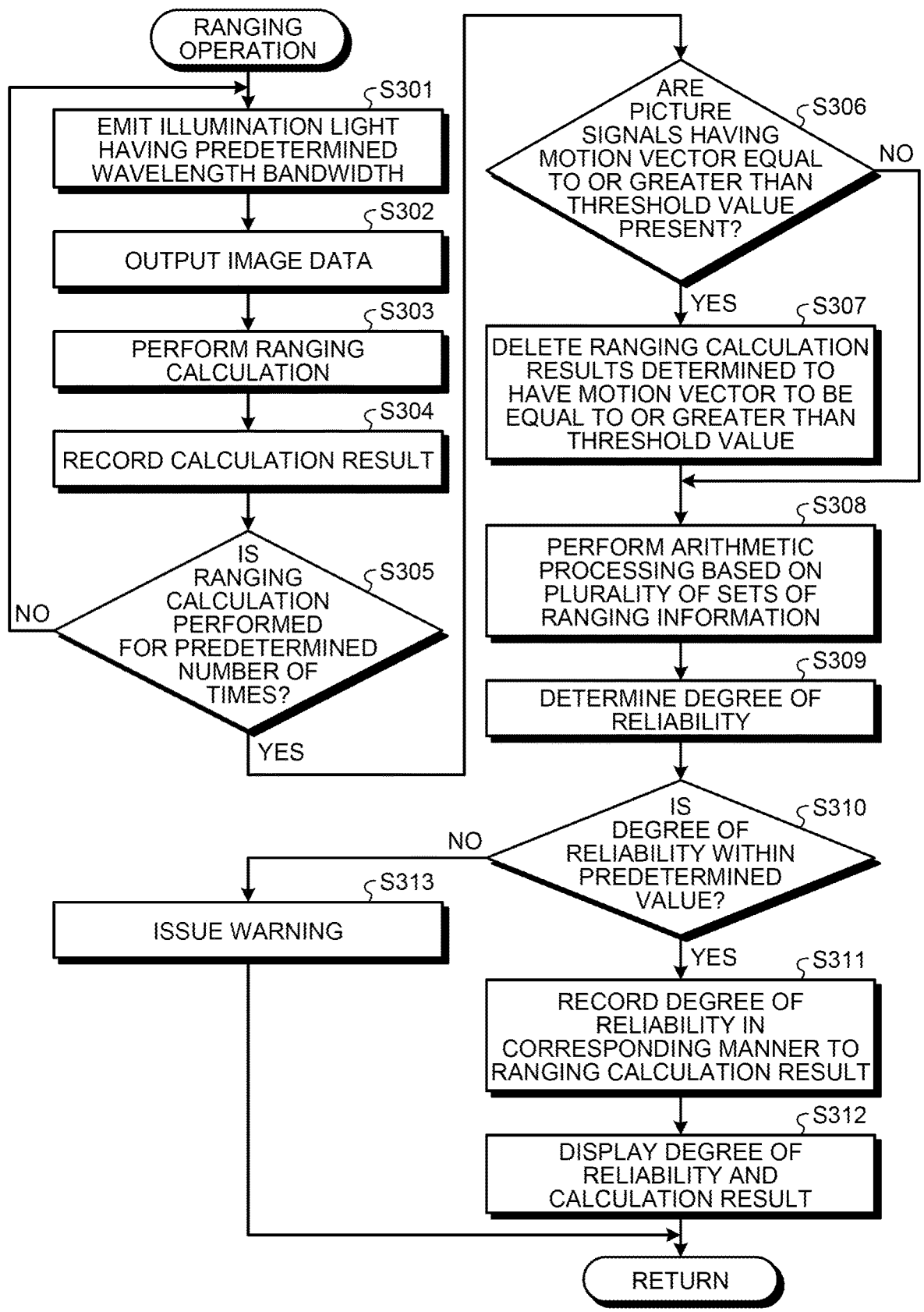
FIG. 21 is a flowchart for explaining the overview of a ranging operation.
Figure 22:
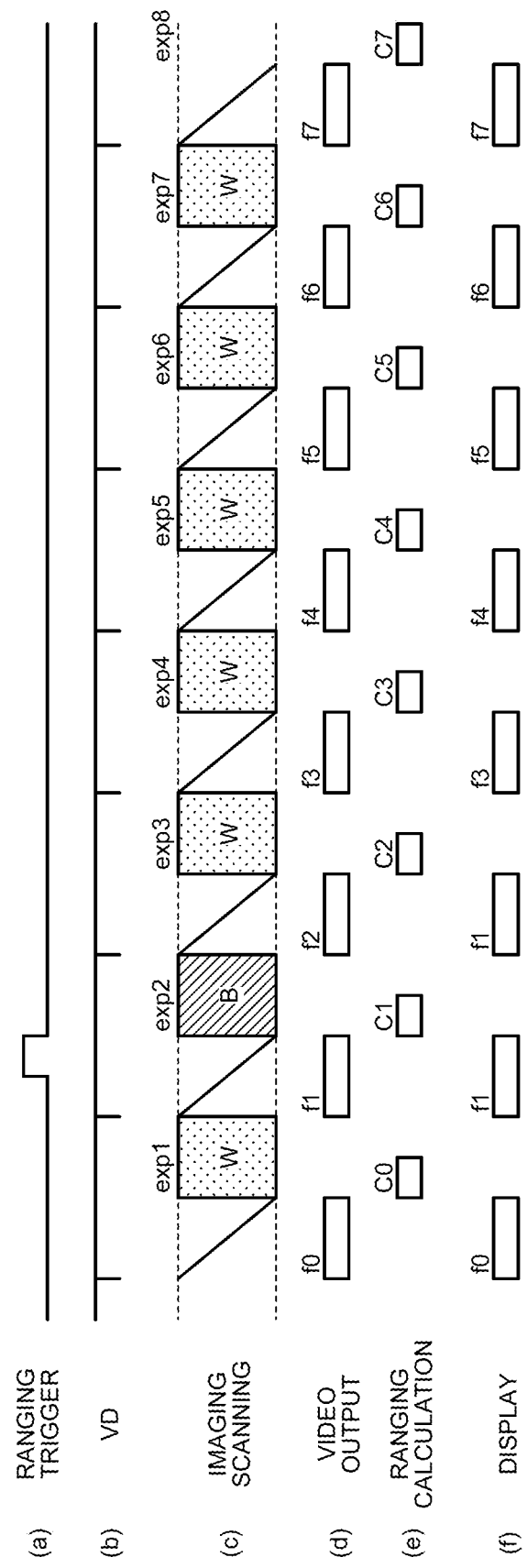
FIG. 22 is a timing chart corresponding to the ranging operation.

Given below is the explanation of the ranging operation performed by the endoscope system 1A. FIG. 21 is a flowchart for explaining the overview of the ranging operation. FIG. 22 is a timing chart corresponding to the ranging operation. In FIG. 22, starting from the top, (a) represents the rising timing of a ranging trigger in the ranging signal; (b) represents the vertical synchronization timing; (c) represents the imaging scanning (exposure period) of the imager 244 and the wavelength bandwidth emitted by the light source device 3; (d) represents the video output timing at which the image data is output from the imager 244; (e) represents the ranging calculation timing; and (f) represents the display timing. Meanwhile, in (c) illustrated in FIG. 22, "W" represents a frame that, when the light source device 3A emits the W light, is exposed to the W light by the imager 244; and "B" represents a frame that, when the light source device 3A emits the B light, is exposed to the B light by the imager 244.

As illustrated in FIG. 21, firstly, the driving control unit 544 causes the light source device 3A emit the illumination light having a predetermined wavelength bandwidth (Step S301); and outputs, to the control device 5, the image data generated by the imager 244 as a result of receiving (getting exposed to) the reflected light coming from the subject (Step S302). More particularly, as illustrated in FIG. 22, firstly, at the point of time of rising of the ranging trigger due to the input of a ranging signal from the operating unit 22 or the input unit 52, the display control unit 545 maintains the display of the display image f1 so that the display image f1 remains displayed in the display device 4. Then, in the state in which the focal position of the optical system 243 is stationary, the driving control unit 544 causes the third light source 314 of the light source device 3A emit the B light. Subsequently, the driving control unit 544 causes the imager 244 receive (for the exposure period exp2) the reflected light of the B light as coming from the subject, and then causes the imager 244 output the imaging image f2 that is based on the image data.

Then, based on the picture signals included in the imaging image f2 input from the imager 244, the arithmetic processing unit 542 performs ranging calculation for calculating the distance from the front end portion 24 of the endoscope device 2 or from the imager 244 to the subject (Step S303), and records the calculation result in the recording unit 53 (Step S304). More particularly, as illustrated in FIG. 22, based on the picture signals included in the imaging image f2 input from the imager 244, the arithmetic processing unit 542 performs ranging calculation and records the calculation result c2 in the recording unit 53.

Then, the processing control unit 54 determines whether or not the ranging calculation has been performed for a predetermined number of times such as once. If it is determined that the ranging calculation has been performed for a predetermined number of times (Yes at Step S305), then the system control proceeds to Step S306 (explained later). On the other hand, if it is determined that the ranging calculation has not been performed for a predetermined number of times (No at Step S307), then the system control returns to Step S301.

The operations performed from Step S306 to Step S308 correspond to the operations performed from Step S207 to Step S209, respectively, illustrated in FIG. 13.

At Step S309, based on the calculation result obtained by the arithmetic processing unit 542 and based on the reference information recorded in the reference information recording unit 532A, the determining unit 543 determines the degree of reliability of the focal position (Step S310). More particularly, based on the calculation result obtained by the arithmetic processing unit 542 and based on the reference information recorded in the reference information recording unit 532A, the determining unit 543 determines the degree of reliability of the calculation result c2 obtained as a result of performing ranging calculation immediately after the input of a ranging trigger.

Figure 23:
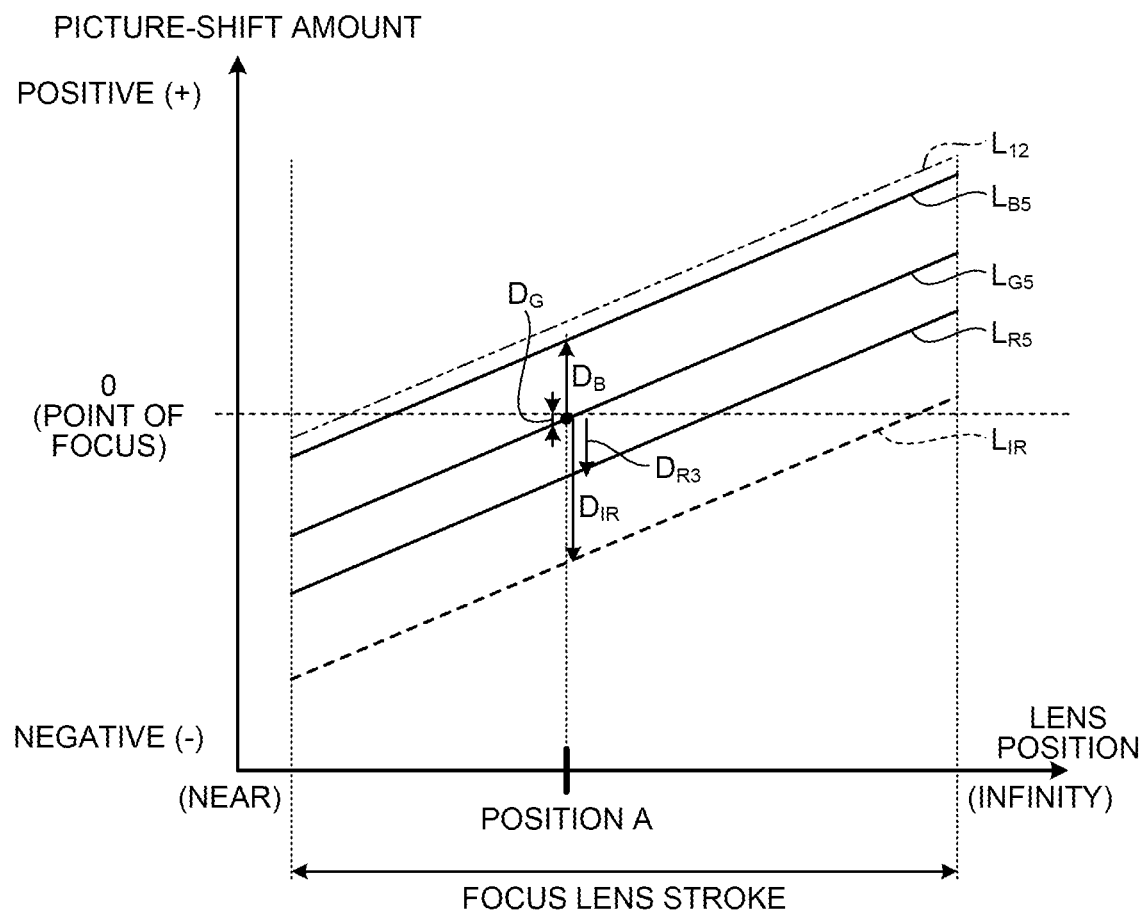
FIG. 23 is a diagram that schematically illustrates the overview of a determination method implemented by the determining unit.

FIG. 23 is a diagram that schematically illustrates the overview of the determination method implemented by the determining unit 543. In FIG. 23, the horizontal axis represents the lens position of the focus lens of the optical system 243, and the vertical axis represents the AF evaluation value (the picture-shift amount). Moreover, in FIG. 23, a straight line $L_{12}$ indicates the picture-shift characteristics based on the variation calculated by the arithmetic processing unit 542.

As illustrated in FIG. 23, firstly, the determining unit 543 determines the degree of coincidence of the straight line $L_{12}$, which is based on the ranging calculation result (for example, the variation or the difference) obtained by the arithmetic processing unit 542, with each of the straight lines $L_{B5}$, $L_{R5}$, and $L_{G5}$; and determines the picture-shift characteristics having the highest degree of coincidence. In the case illustrated in FIG. 23, the determining unit 543 determines that the straight lines $L_{12}$ and $L_{B5}$ have the highest degree of coincidence. Then, the determining unit 543 determines (calculates) the degree of coincidence between the straight lines $L_{12}$ and $L_{B5}$ the degree of reliability, as well as determines the subject distance to be equal to 5 mm.

The operations performed from Step S310 to Step S313 correspond to the operations performed from Step S211 to Step S214, respectively. After the operation at Step S312 or Step S313 is performed, the system control returns to the main routine illustrated in FIG. 12.

According to the second embodiment described above, the arithmetic processing unit 542 obtains the ranging calculation result attributed to the changes in the focal position occurring due to the switching of the wavelength bandwidth of the light emitted by the light source device 3. That enables achieving enhancement in the accuracy of the ranging calculation.

First Modification Example of Second Embodiment

Given below is the explanation of a first modification example of the second embodiment. In the second embodiment described above, the B light is emitted at the time of performing ranging. Alternatively, in the first modification example of the second embodiment, lights having difference wavelength bandwidths are sequentially emitted at the time of performing ranging. The endoscope system according to the first modification example of the second embodiment has an identical configuration to the endoscope system 1A according to the second embodiment, and only the calculation method during the ranging operation is different. Thus, the other operations are identical. The following explanation is given about the main part of the calculation method during the ranging operation performed in the endoscope system according to the first modification example of the second embodiment. The configuration identical to the endoscope system 1A according to the second embodiment is referred to by the same reference numerals, and the detailed explanation is not given again.

Ranging Operation

Figure 24:
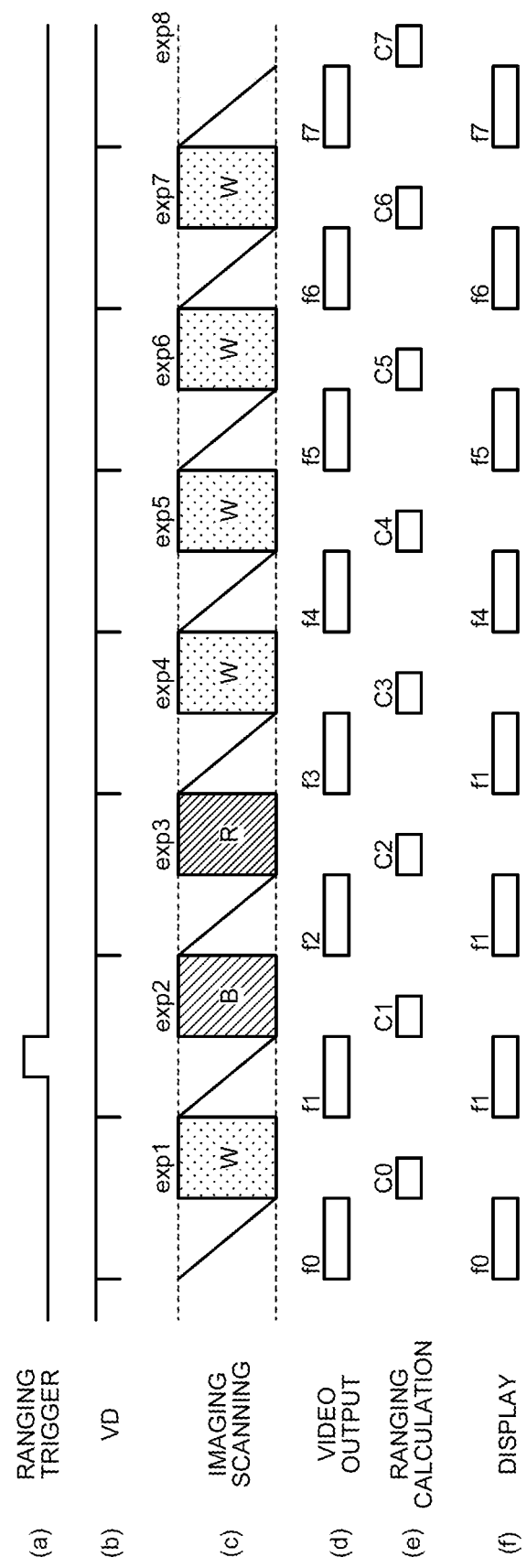
FIGS. 24 and 25 are timing charts corresponding to the ranging operation.

FIG. 24 is a timing chart corresponding to the ranging operation. In FIG. 24, starting from the top, (a) represents the rising timing of a ranging trigger in the ranging signal; (b) represents the vertical synchronization timing; (c) represents the imaging scanning (exposure period) of the imager 244 and the wavelength bandwidth emitted by the light source device 3A; (d) represents the video output timing at which the image data is output from the imager 244; (e) represents the ranging calculation timing; and (f) represents the display timing. Meanwhile, in (c) illustrated in FIG. 24, "W" represents a frame that, when the light source device 3A emits the W light, is exposed to the W light by the imager 244; "B" represents a frame that, when the light source device 3A emits the B light, is exposed to the B light by the imager 244; and "R" represents a frame that, when the light source device 3A emits the R light, is exposed to the R light by the imager 244.

As illustrated in FIG. 24, at the point of time of rising of the ranging trigger due to the input of a ranging signal from the operating unit 22 or the input unit 52, the display control unit 545 maintains the display of the display image f1 so that the display image f1 remains displayed in the display device 4. Then, in the state in which the focal position of the optical system 243 is stationary, the driving control unit 544 causes the third light source 314 of the light source device 3A emit the B light. Subsequently, the driving control unit 544 causes the imager 244 receive (for the exposure period exp2) the reflected light of the B light as coming from the subject, and then causes the imager 244 output the imaging image f2 that is based on the image data. Moreover, based on the picture signals included in the imaging image f2 input from the imager 244, the arithmetic processing unit 542 performs ranging calculation for calculating the distance from the front end portion 24 of the endoscope device 2 or from the imager 244 to the subject, and records the calculation result c2 in the recording unit 53A.

Then, in the state in which the focal position of the optical system 243 is stationary, the driving control unit 544 causes the first light source 312 of the light source device 3A emit the R light. Subsequently, the driving control unit 544 causes the imager 244 receive (for the exposure period exp3) the reflected light of the R light as coming from the subject, and then causes the imager 244 output the imaging image f3 that is based on the image data. Then, based on the picture signals included in the imaging image f3 input from the imager 244, the arithmetic processing unit 542 performs ranging calculation for calculating the distance from the front end portion 24 of the endoscope device 2 or from the imager 244 to the subject, and records the calculation result c3 in the recording unit 53A.

Subsequently, the determining unit 543 determines the degree of reliability of the focal position based on the following: the calculation result c1 recorded in the recording unit 53A and obtained as a result of performing ranging calculation during the normal observation (the W light); the calculation result c2 regarding the B light as recorded in the recording unit 53A; the calculation result c3 regarding the R light as recorded in the recording unit 53A; and the reference information recorded in the reference information recording unit 532A.

Then, the display control unit 545 updates the display frames (f4 to f7) of the display image displayed in the display device 4.

According to the first modification example of the second embodiment, based on the reference information that is recorded in the reference information recording unit 532A and that is associated to each wavelength bandwidth of a narrow-bandwidth light and based on the ranging calculation result obtained by the arithmetic processing unit 542, the determining unit 543 determines the degree of reliability of the ranging information at the point of time of input of a ranging trigger. That enables achieving enhancement in the accuracy of the ranging calculation.

Meanwhile, in the first modification example of the second embodiment, the light source device 3A is made to emit the W light, the B light, and the R light, respectively. However, when the phase difference pixels 71 are placed at the positions of the R pixels, the G pixels, and the B pixels; the driving control unit 544 can control the illumination control unit 33 so as to cause the light source device 3A emit the B light and the G light in the first frame and emit the G light and the IR light (the A light) in the second frame in that order. Of course, when the phase difference pixels 71 are placed only at the positions of the G pixels, the driving control unit 544 can control the illumination control unit 33 to cause the light source device 3A emit the G light.

Second Modification Example of Second Embodiment

Given below is the explanation of a second modification example of the second embodiment. In the second embodiment described above, the image signals are read from all pixels of the imager 244. In contrast, in the second modification example of the second embodiment, picture signals are read only from the phase difference pixels 71, so that the imaging can be speeded up. The endoscope system according to the second modification example of the second embodiment has an identical configuration to the endoscope system 1A according to the second embodiment, and only the timings in the ranging operation are different. The following explanation is given about the main part of the ranging operation performed in the endoscope system according to the second modification example of the second embodiment. The configuration identical to the endoscope system 1A according to the second embodiment is referred to by the same reference numerals, and the detailed explanation is not given again.

Ranging Operation

Figure 25:
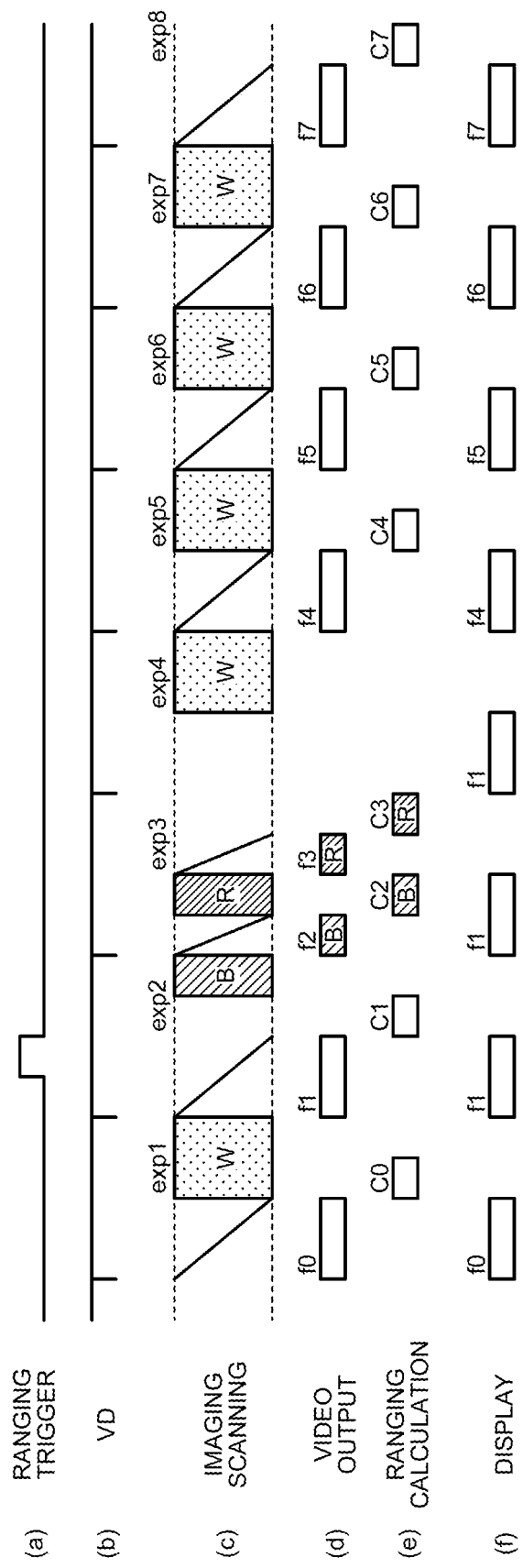

FIG. 25 is a timing chart corresponding to the ranging operation. In FIG. 25, starting from the top, (a) represents the rising timing of a ranging trigger in the ranging signal; (b) represents the vertical synchronization timing; (c) represents the imaging scanning (exposure period) of the imager 244 and the wavelength bandwidth emitted by the light source device 3A; (d) represents the video output timing at which the image data is output from the imager 244; (e) represents the ranging calculation timing; and (f) represents the display timing. In (c) illustrated in FIG. 25, "W" represents a frame that, when the light source device 3A emits the W light, is exposed to the W light by the imager 244; "B" represents a frame that, when the light source device 3A emits the B light, is exposed to the B light by the imager 244; and "R" represents a frame that, when the light source device 3A emits the R light, is exposed to the R light by the imager 244.

As illustrated in FIG. 22, firstly, at the point of time of rising of the ranging trigger due to the input of a ranging signal from the operating unit 22 or the input unit 52, the display control unit 545 maintains the display of the display image f1 so that the display image f1 remains displayed in the display device 4. Then, in the state in which the focal position of the optical system 243 is stationary, the driving control unit 544 controls the illumination control unit 33 and causes the third light source 314 of the light source device 3A emit the B light. Then, the driving control unit 544 controls the imaging control unit 65 and causes the imager 244 receive (for the exposure period exp2) the reflected light of the B light as coming from the subject, and ensures that the imaging image f2 that is based on the picture signals is output only from the phase difference pixels in the imager 244. Moreover, based on the imaging image f2 input from the imager 244, the arithmetic processing unit 542 performs ranging calculation for calculating the distance from the front end portion 24 of the endoscope device 2 or from the imager 244 to the subject, and records the calculation result c2 in the recording unit 53A.

Subsequently, the driving control unit 544 controls the illumination control unit 33 so that, in the state in which the focal position of the optical system 243 is stationary, the first light source 312 of the light source device 3A is made to emit the R light. Then, the driving control unit 544 controls the imaging control unit 65 and causes the imager 244 receive (for the exposure period exp3) the reflected light of the R light as coming from the subject, and ensures that the imaging image f3 that is based on the picture signals is output only from the phase difference pixels of the imager 244. Moreover, based on the imaging image f3 input from the imager 244, the arithmetic processing unit 542 performs ranging calculation for calculating the distance from the front end portion 24 of the endoscope device 2 or from the imager 244 to the subject, and records the calculation result c3 in the recording unit 53A.

Subsequently, the determining unit 543 determines the degree of reliability of the focal position based on the following: the calculation result c1 that is recorded in the recording unit 53A and that is obtained as a result of performing ranging calculation during the normal observation (the W light); the calculation result c2 regarding the B light as recorded in the recording unit 53A; the calculation result c3 regarding the R light as recorded in the recording unit 53A; and the reference information recorded in the reference information recording unit 532A.

Then, the display control unit 545 updates the display frames (f4 to f7) of the display image displayed in the display device 4.

According to the second modification example of the second embodiment, since only the phase difference data attributed to the phase difference pixels 71 is read, the reading from the imager 244 can be speeded up. As a result, the light-emission time difference among different light sources and the frame-reading time difference become smaller, thereby enabling achieving reduction in the impact of picture blurring and camera shake. Hence, the accuracy of the ranging calculation can be enhanced.

Third Embodiment

Given below is the explanation of a third embodiment. In the first embodiment described earlier, the image signals are read from all pixels of the imager 244. In contrast, in the third embodiment, the picture signals are read only from the phase difference pixels, so that the imaging can be speeded up. The endoscope system according to the third embodiment has an identical configuration to the endoscope system 1 according to the first embodiment, and only the method for reading the image signals and the picture signals from the imager during the ranging operation is different. The following explanation is given about the overview of the method for reading the image signals and the picture signals from the imager during the ranging operation that is performed in the endoscope system according to the third embodiment. The configuration identical to the endoscope system 1 according to the first embodiment is referred to by the same reference numerals, and the detailed explanation is not given again.

Ranging Operation

Figure 27:
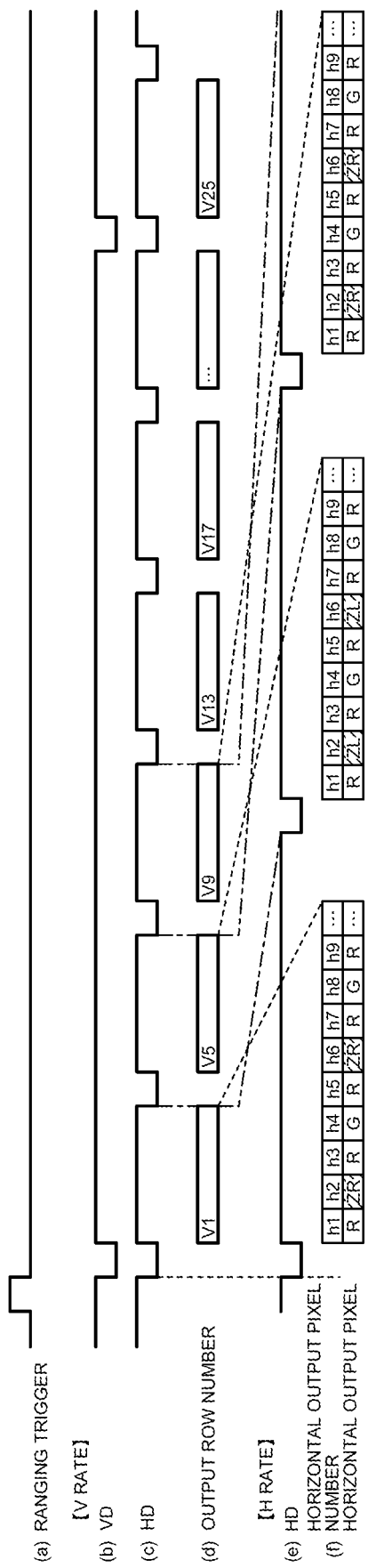
FIG. 27 is a timing chart corresponding to a ranging operation performed in the endoscope system according to the third embodiment.

FIG. 26 is a diagram that schematically illustrates the pixel layout of the imager 244 according to the third embodiment. FIG. 27 is a timing chart corresponding to the ranging operation performed in the endoscope system 1 according to the third embodiment. In FIG. 27, starting from the top, (a) represents the rising timing of a ranging trigger in the ranging signal; (b) represents the vertical synchronization timing; (c) represents the horizontal synchronization timing; (d) represents the output row signal; (e) represents the expansion of the horizontal synchronization timing period of (c); and (f) represents the horizontal output pixel number and the horizontal output pixel.

As illustrated in FIGS. 26 and 27, at the point of time of rising of the ranging trigger due to the input of a ranging signal from the operating unit 22 or the input unit 52, the driving control unit 544 controls the imaging control unit 65 and, from the horizontal lines in which the phase difference pixels 71 are arranged, reads picture signals from the phase difference pixels 71 and reads the image signals from the imaging pixels 70. For example, as illustrated in FIG. 27, the imager 244 has the phase difference pixels 71 arranged in the cycle of four rows. Hence, by controlling the imaging control unit 65, as compared to the time required for reading the image signals from all pixels of the imager 244, the driving control unit 544 becomes able to shorten, by one-fourth, the time required for reading the image signals and the pixel signals only from the horizontal lines in which the phase difference pixels 71 are arranged. More particularly, when all-pixel reading of the imager 244 is performed at 120 Hz scanning (8.3 ms), the driving control unit 544 can control the imaging control unit 65 and read, at 480 Hz scanning (2 ms), the image signals and the picture signals only from the horizontal lines in which the phase difference pixels 71 are arranged. Meanwhile, the driving control unit 544 determines the degree of reliability of the ranging information by performing identical operations to the first embodiment or the second embodiment, that is, by performing ranging according to a plurality of focal positions attributed to the movement of the optical system 243 or by performing ranging according to the emission of a narrow-bandwidth light from the light source device 3A.

According to the third embodiment described above, since the driving control unit 544 reads, from the horizontal lines in which the phase difference pixels 71 are arranged, the picture signals from the phase difference pixels 71 and the image signals from the imaging pixels, the reading from the imager 244 can be speeded up. As a result, the light-emission time difference among different light sources and the frame-reading time difference become smaller, thereby enabling achieving reduction in the impact of picture blurring and camera shake.

Moreover, according to the third embodiment, since the driving control unit 544 reads, from the horizontal lines in which the phase difference pixels 71 are arranged, the picture signals from the phase difference pixels 71 and the image signals from the imaging pixels, the stoppage period of the ranging calculation frame can be shortened.

First Modification Example of Third Embodiment

Given below is the explanation of a first modification example of the third embodiment. In the third embodiment described above, the image signals are read only from the horizontal lines in which the phase difference pixels are arranged. Instead, the light emission cycle of the light emitted by the light source device 3A is changed. Herein, the configuration identical to the endoscope system 1A according to the second embodiment is referred to by the same reference numerals, and the detailed explanation is not given again.

Figure 28:
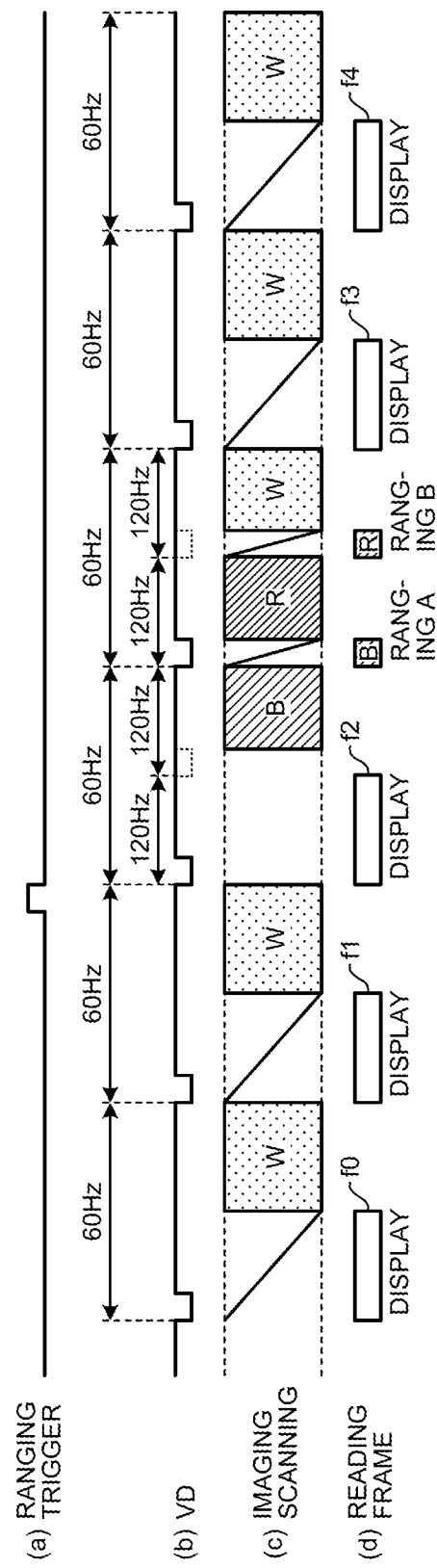
FIG. 28 is a timing chart corresponding to a ranging operation according to a first modification example of the third embodiment.

FIG. 28 is a timing chart corresponding to the ranging operation according to the first modification example of the third embodiment. In FIG. 28, starting from the top, (a) represents the rising timing of a ranging trigger; (b) represents the vertical synchronization timing; (c) represents the imaging scanning timing of the imager 244; and (d) represents the display frame read from the imager 244.

As illustrated in FIG. 28, at the point of time of rising of the ranging trigger due to the input of a ranging signal from the operating unit 22 or the input unit 52, the driving control unit 544 controls the illumination control unit 33 and causes the light source device 3A emit the B light, the R light, and the W light in that order at the intervals of 120 Hz. Moreover, the driving control unit 544 controls the imaging control unit 65 and changes the imaging timing of the imager 244 from 60 Hz to 120 Hz. Meanwhile, the determining unit 543 determines the degree of reliability of the ranging information by performing ranging according to the emission of a narrow-bandwidth light from the light source device 3A in an identical manner to the second embodiment.

According to the first modification example of the third embodiment, since the reading from the imager 244 can be speeded up, the light-emission time difference among different light sources and the frame-reading time difference become smaller, thereby enabling achieving reduction in the impact of picture blurring and camera shake.

Second Modification Example of Third Embodiment

Figure 29:
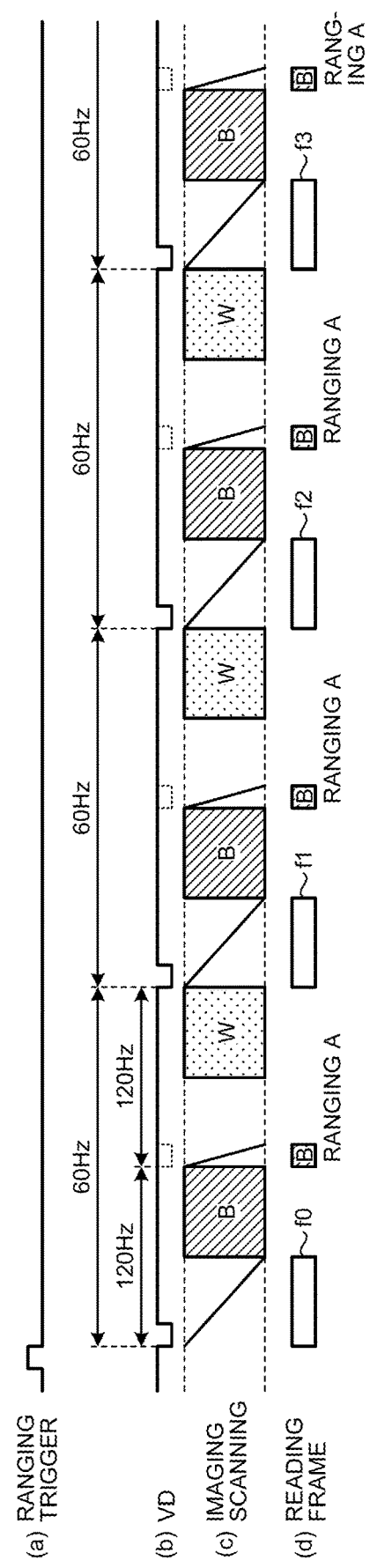
FIG. 29 is a timing chart corresponding to a ranging operation according to a second modification example of the third embodiment.

Given below is the explanation of a second modification example of the third embodiment. In the second modification example of the third embodiment, the light source device is made to alternately emit the W light and a narrow-bandwidth light, and the image signals of the imaging pixels and the picture signals of the phase difference pixels are alternately read. Meanwhile, the configuration identical to the endoscope system 1A according to the second embodiment is referred to by the same reference numerals, and the detailed explanation is not given again.
Ranging Operation FIG. 29 is a timing chart corresponding to the ranging operation according to the second modification example of the third embodiment. In FIG. 29, starting from the top, (a) represents the rising timing of a ranging trigger; (b) represents the vertical synchronization timing; (c) represents the imaging scanning timing of the imager 244; and (d) represents the display frame read from the imager 244.

As illustrated in FIG. 29, at the point of time of rising of the ranging trigger due to the input of a ranging signal from the operating unit 22 or the input unit 52, the driving control unit 544 controls the illumination control unit 33 and causes the light source device 3A alternately emit the B light and the W light at the intervals of 120 Hz. Moreover, the driving control unit 544 controls the imaging control unit 65 and changes the imaging timing of the imager 244 from 60 Hz to 120 Hz, and ensures that the picture signals of the phase difference pixels 71 and the image signals of the imaging pixels 70 are alternately output.

According to the second modification example of the third embodiment, since the reading from the imager 244 can be speeded up, the light-emission time difference among different light sources and the frame-reading time difference become smaller, thereby enabling achieving reduction in the impact of picture blurring and camera shake.

Third Modification Example of Third Embodiment

Figure 30:
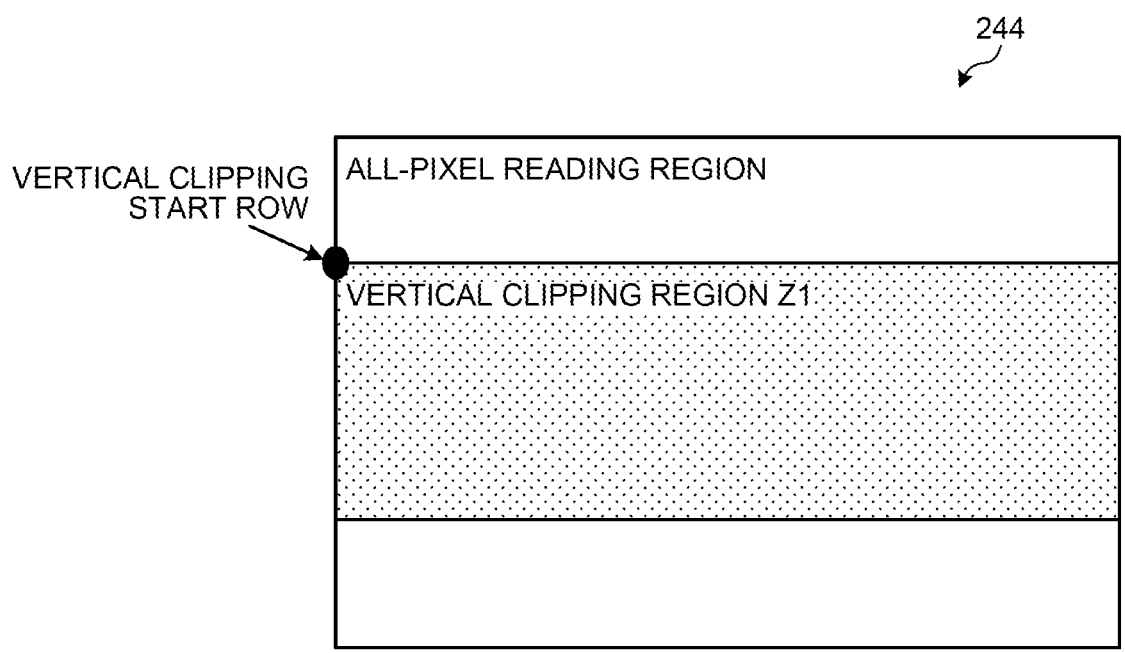
FIG. 30 is a diagram that schematically illustrates a reading region of the imager.
Figure 31:
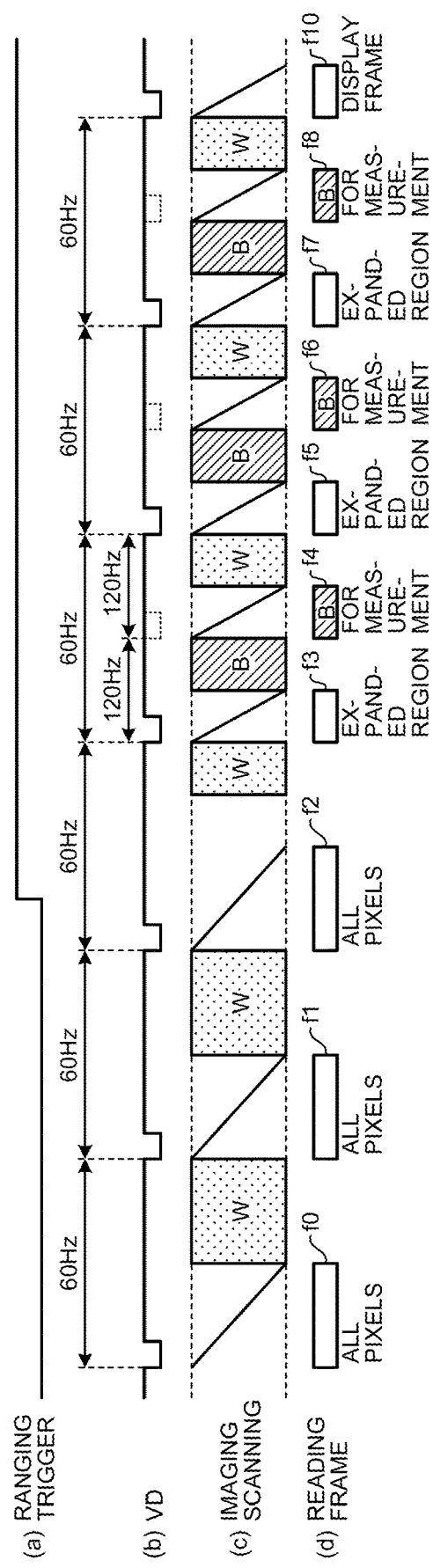
FIG. 31 is a timing chart corresponding to a ranging operation according to a third modification example of the third embodiment.

Given below is the explanation of a third modification example of the third embodiment. In the third modification example of the third embodiment, a reading range is set for reading the image signals from the imager 244, and the image signals are read from within the set reading range. Meanwhile, the configuration identical to the endoscope system 1A according to the second embodiment is referred to by the same reference numerals, and the detailed explanation is not given again.
Ranging Operation FIG. 30 is a diagram that schematically illustrates a reading region of the imager 244. FIG. 31 is a timing chart corresponding to the ranging operation according to the third modification example of the third embodiment. In FIG. 31, starting from the top, (a) represents the rising timing of a ranging trigger; (b) represents the vertical synchronization timing; (c) represents the imaging scanning timing of the imager 244; and (d) represents the display frame read from the imager 244.

As illustrated in FIGS. 30 and 31, when a specification signal for specifying the display region is input from the operating unit 22 or the input unit 52 and at the point of time of rising of the ranging trigger due to the input of a ranging signal from the operating unit 22 or the input unit 52, the driving control unit 544 controls the illumination control unit 33 and causes the light source device 3A alternately emit the W light and the B light in that order for a predetermined number of times at the interval of 120 Hz. Moreover, the driving control unit 544 controls the imaging control unit 65 and changes the imaging timing of the imager 244 from 60 Hz to 120 Hz. Meanwhile, the determining unit 543 determines the degree of reliability of the ranging information by performing ranging according to the emission of a narrow-bandwidth light from the light source device 3A in an identical manner to the second embodiment.

According to the third modification example of the third embodiment, since the reading from the imager 244 can be speeded up, the light-emission time difference among different light sources and the frame-reading time difference become smaller, thereby enabling achieving reduction in the impact of picture blurring and camera shake.

Fourth Embodiment

Figure 32:
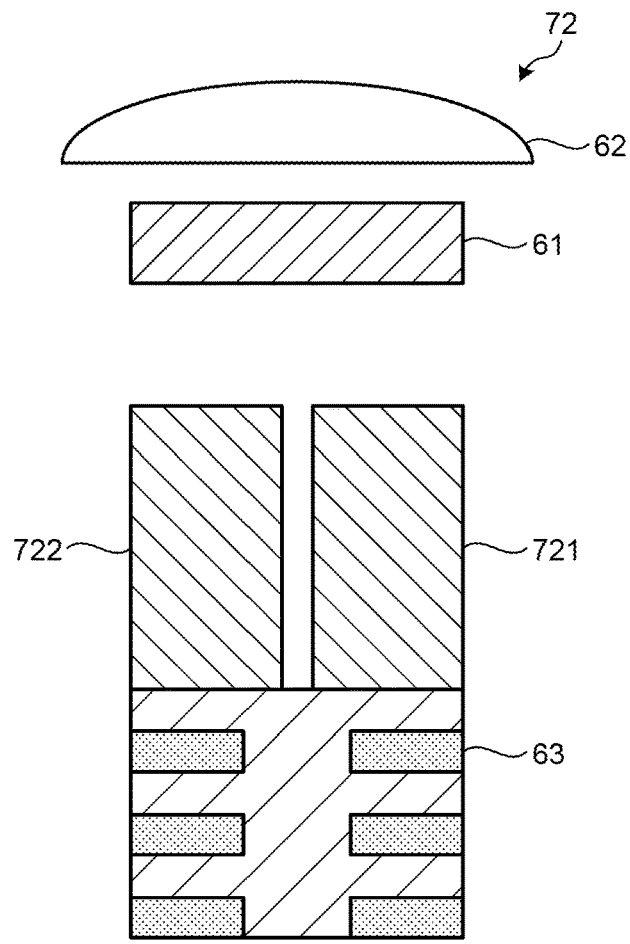
FIG. 32 is a cross-sectional view of a phase difference pixel according to a fourth embodiment.
Figure 33:
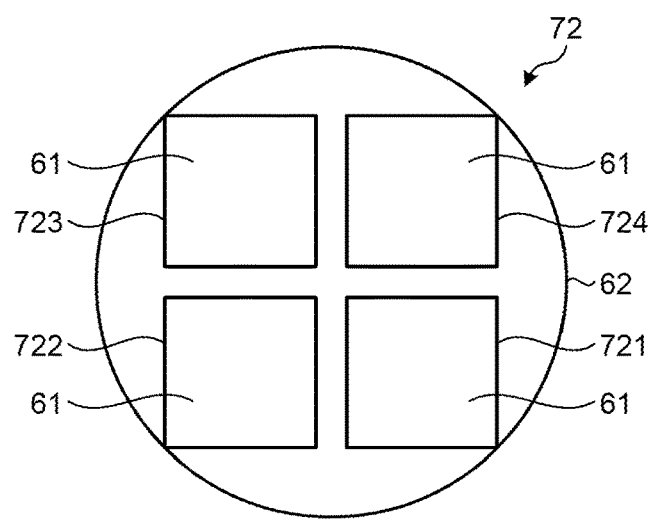
FIG. 33 is a top view of a phase difference pixel according to the fourth embodiment.

Given below is the explanation of a fourth embodiment. In the first to third embodiments, the pairs of right and left phase difference pixels are provided that have the light shielding portions 711R and 711L on the right and left sides in the light receiving region of a pixel. In contrast, in a fourth embodiment, divided pixels obtained by dividing the light receiving region of a pixel are provided as phase difference pixels. In the following explanation, a configuration of the phase difference pixels according to the fourth embodiment is explained, and that is followed by the explanation of the ranging operation performed in the endoscope system according to the fourth embodiment. Meanwhile, the configuration identical to the endoscope system 1 according to the first embodiment is referred to by the same reference numerals, and the detailed explanation is not given again.
Configuration of Phase Difference Pixel FIG. 32 is a cross-sectional view of a phase difference pixel according to the fourth embodiment. FIG. 33 is a top view of a phase difference pixel according to the fourth embodiment.

A phase difference pixel 72 illustrated in FIGS. 32 and 33 is formed by arranging the following in the given order: four light receiving portions 721 to 724 being made of photodiodes and functioning as photoelectric conversion elements, the color filter 61, and the micro lens 62. Moreover, on the rear surface of the four light receiving portions 721 to 724, the reading unit 63 is formed in a laminated manner.

Figure 34:
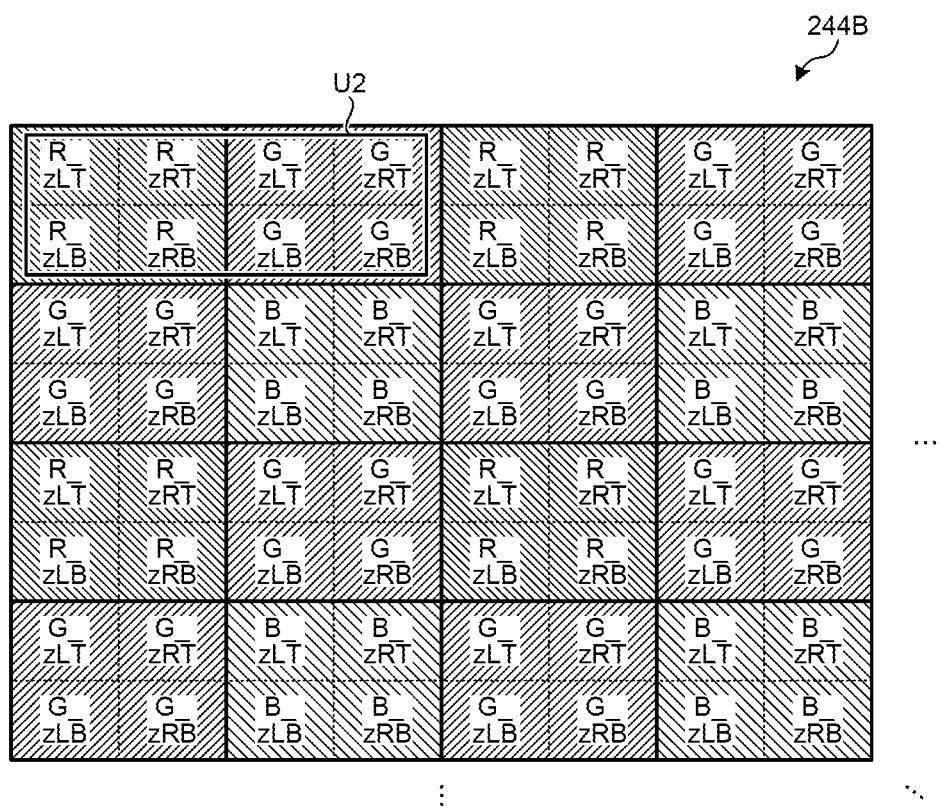
FIG. 34 is a diagram that schematically illustrates a layout of the imager according to the fourth embodiment.

The phase difference pixel 72 configured in the manner explained above generates sets of four pixel signals (electric signals) meant for adjustment of the focal position and for ranging, and outputs them as the picture signals.
Configuration of Imager FIG. 34 is a diagram that schematically illustrates a layout of the imager according to the fourth embodiment. In an imager 244B illustrated in FIG. 34, the four light receiving portions 721 to 724 are configured as single unit pixels, and four unit pixels are treated as a single unit U2. On the light receiving surface of each unit pixel, any one filter in the Bayer layout is arranged. In FIG. 34, the pixels in which the red filter R is arranged are referred to as "R_zLT", "R_zRT", "R_zRB", and "R_zLB" in the clockwise direction with reference to the top left pixel. Similarly, the pixels in which the green filter G is arranged are referred to as "G_zLT", "G_zRT", "G_zRB", and "G_zLB" in the clockwise direction with reference to the top left pixel. Moreover, the pixels in which the blue filter B is arranged are referred to as "B_zLT", "B_zRT", "B_zRB", and "B_zLB" in the clockwise direction with reference to the top left pixel.

Ranging Operation

Figure 35:
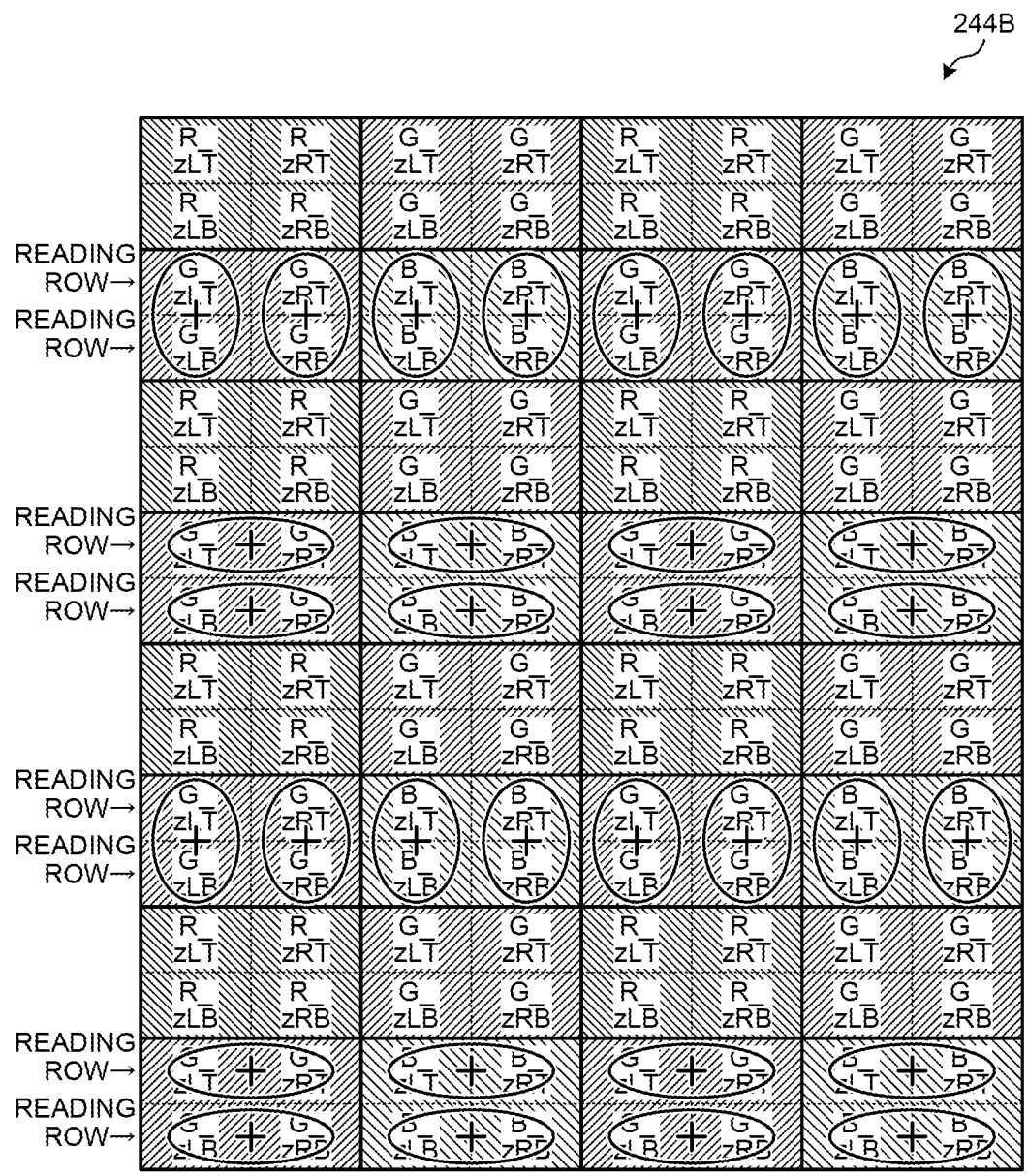
FIG. 35 is a diagram that schematically illustrates a method for reading the imager when a light source device emits light having the wavelength bandwidth of a short wavelength.
Figure 36:
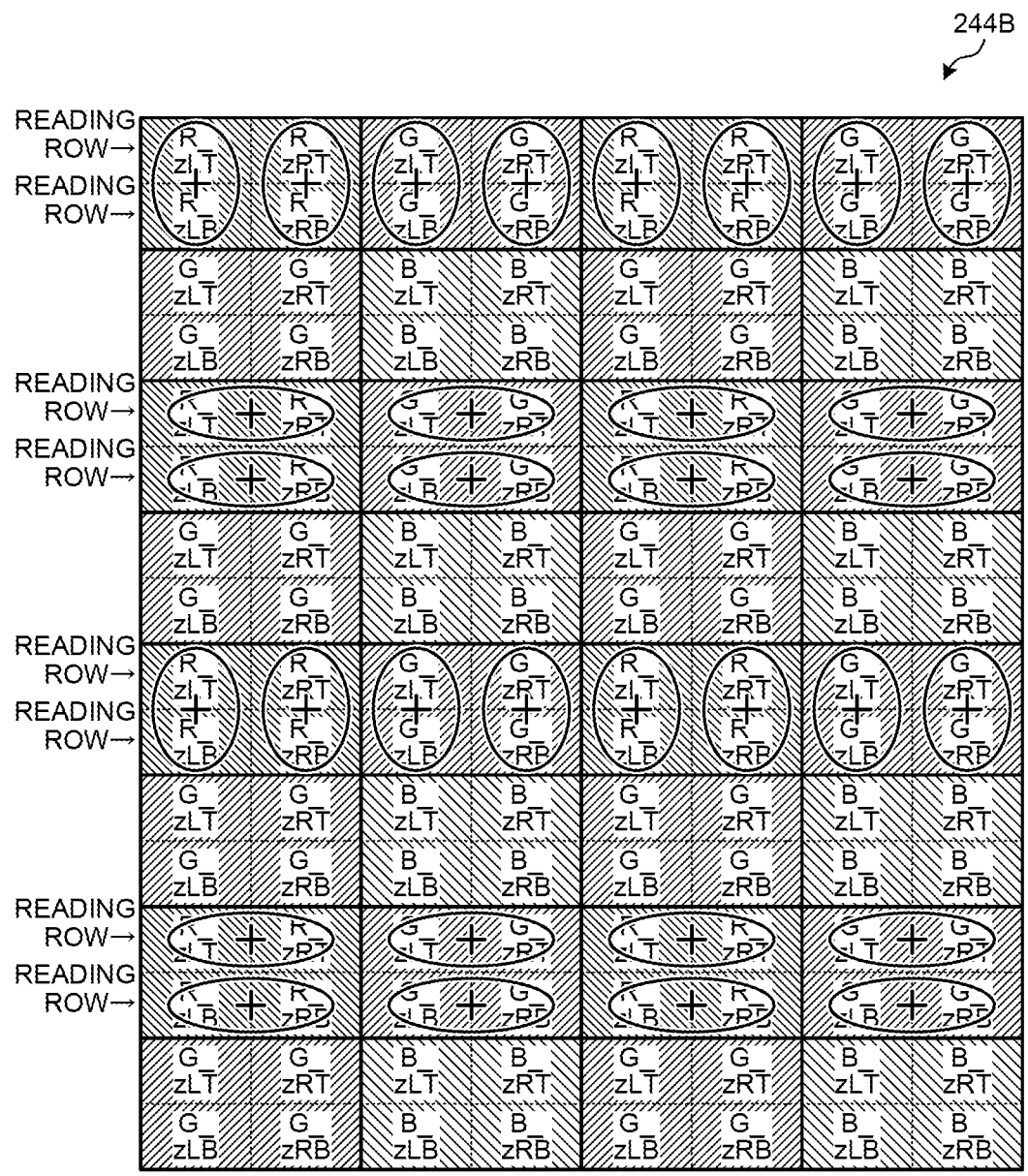
FIG. 36 is a diagram that schematically illustrates a method for reading the imager when the light source device emits light having the wavelength bandwidth of a long wavelength.

Given below is the explanation of a method for reading from the imager during the ranging operation performed in the endoscope system 1 according to the fourth embodiment. FIG. 35 is a diagram that schematically illustrates the method for reading the imager when the light source device 3 emits light having the wavelength bandwidth of a short wavelength. FIG. 36 is a diagram that schematically illustrates the method for reading the imager when the light source device 3 emits light having the wavelength bandwidth of a long wavelength.

As illustrated in FIG. 35, at the point of time of rising of the ranging trigger due to the input of a ranging signal from the operating unit 22 or the input unit 52, the driving control unit 544 controls the illumination control unit 33; and, when the light source device 3 emits the B light having a short wavelength, controls the imaging control unit 65 and, in the odd-numbered rows among the reading rows in the imager 244B, adds the pixel signals of the left-side pixels and adds the pixel signals of the right-side pixels. Moreover, as a result of controlling the imaging control unit 65, in the even-numbered rows among the reading rows in the imager 244B, the driving control unit 544 adds the pixel signals of the upper-side pixels and adds the pixel signals of the lower-side pixels. More particularly, as a result of controlling the imaging control unit 65, in the odd-numbered rows among the reading rows in the imager 244B, the driving control unit 544 adds the pixel signals of the left-side pixels (i.e., G_zLT+G_zLB or B_zLT+B_zLB) and adds the pixel signals of the right-side pixels (i.e., G_zRT+G_zRB or B_zRT+B_zRB). Moreover, as a result of controlling the imaging control unit 65, in the even-numbered rows among the reading rows in the imager 244B, the driving control unit 544 adds the pixel signals of the upper-side pixels (i.e., G_zLT+G_zRT or B_zLT+B_zRT) and adds the pixel signals of the lower-side pixels (i.e., G_zLB+G_zRB or B_zLB+B_zRB). Consequently, the arithmetic processing unit 542 performs cross ranging.

Moreover, as illustrated in FIG. 36, at the point of time of rising of the ranging trigger due to the input of a ranging signal from the operating unit 22 or the input unit 52, when the light source device 3 emits the R light having a long wavelength, the driving control unit 544 controls the imaging control unit 65 and, in the odd-numbered rows among the reading rows, adds the pixel signals of the left-side pixels and adds the pixel signals of the right-side pixels. Moreover, as a result of controlling the imaging control unit 65, in the even-numbered rows among the reading rows, the driving control unit 544 adds the pixel signals of the upper-side pixels and adds the pixel signals of the lower-side pixels. More particularly, as a result of controlling the imaging control unit 65, in the odd-numbered rows among the reading rows in the imager 244B, the driving control unit 544 adds the pixel signals of the left-side pixels (i.e., R_zLT+R_zLB or G_zLT+G_zLB) and adds the pixel signals of the right-side pixels (i.e., G_zRT+G_zRB or G_zRT+G_zRB). Moreover, as a result of controlling the imaging control unit 65, in the even-numbered rows among the reading rows in the imager 244B, the driving control unit 544 adds the pixel signals of the upper-side pixels (i.e., R_zLT+R_zRT or G_zLT+G_zRT) and adds the pixel signals of the lower-side pixels (i.e., R_zLB+R_zRB or G_zLB+G_zRB). Consequently, the arithmetic processing unit 542 performs cross ranging.

According to the fourth embodiment described above, the driving control unit 544 adds the picture signals of the phase difference pixels 71 on the right and left sides, or adds the picture signals of the phase difference pixels 71 on the upper and lower sides, and outputs the picture signals. As a result, the reading speed of the imager 244 can be enhanced.

Figure 37:
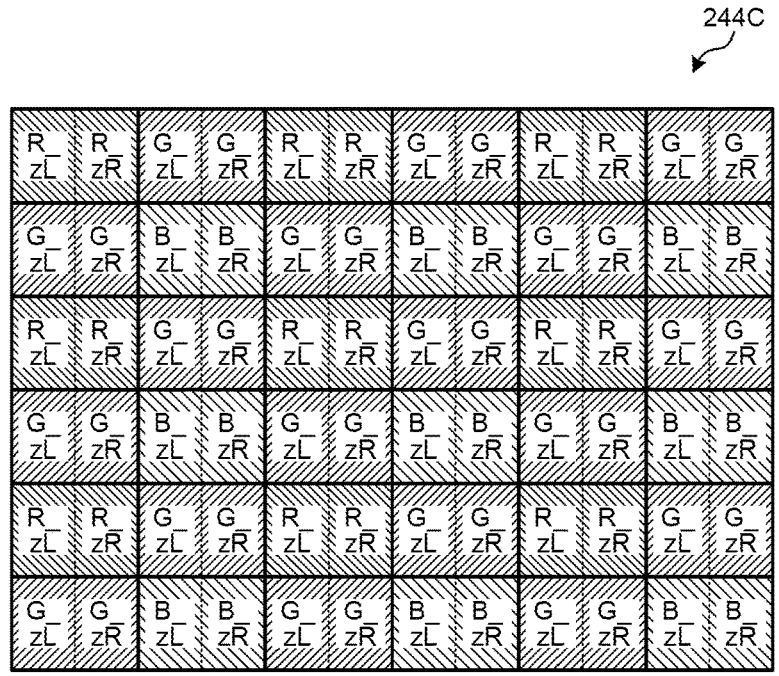
FIGS. 37 and 38 are diagrams that schematically illustrate other layouts of the imager according to the fourth embodiment.
Figure 38:
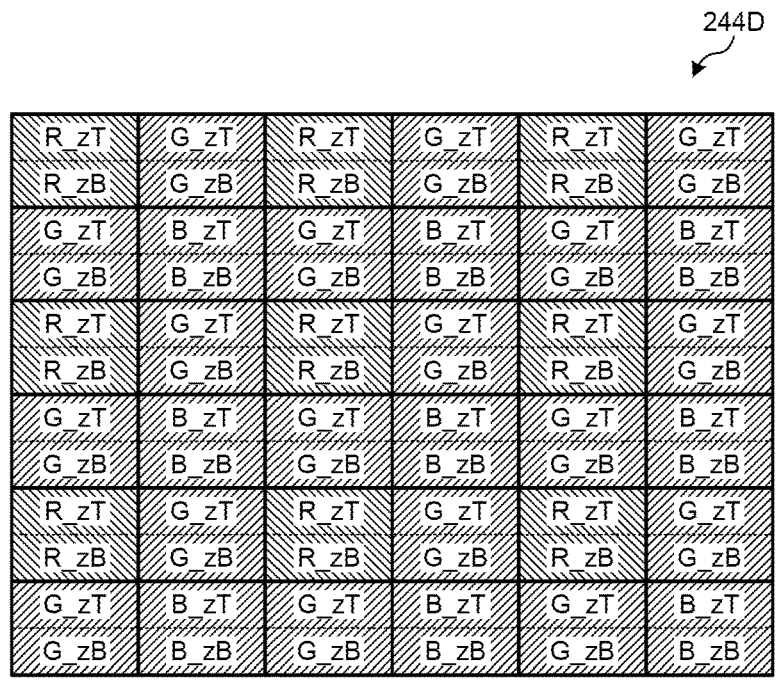

Meanwhile, in the fourth embodiment, the four light receiving portions 721 to 724 are treated as single unit pixels. Alternatively, as illustrated in an imager 244C in FIG. 37, a pair of right and left light receiving portions can be treated as a single unit pixel. Still alternatively, as illustrated in an imager 244D in FIG. 38, a pair of upper and lower light receiving portions can be treated as a single unit pixel.

Fifth Embodiment

Given below is the explanation of a fifth embodiment. In the first to fourth embodiments, the color filter is configured using the Bayer layout. In contrast, in the fifth embodiment, the color filter is configured also using cyan filters in some part of it. Meanwhile, the configuration identical to the endoscope system 1 according to the first embodiment is referred to by the same reference numerals, and the detailed explanation is not given again.

Configuration of Color Filter

Figure 39:
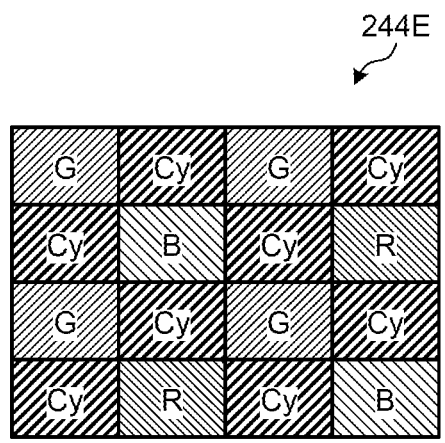
FIG. 39 is a diagram that schematically illustrates a configuration of the color filter according to a fifth embodiment.

FIG. 39 is a diagram that schematically illustrates a configuration of the color filter according to the fifth embodiment. A color filter 61E illustrated in FIG. 39 is configured using either one of the blue filter B and the red filter R, along with the green filter G and two cyan filters C. The cyan filters Cy transmit at least two or more lights including the light having the wavelength bandwidth of the blue color and the light having the wavelength bandwidth of the green color.

Figure 40:
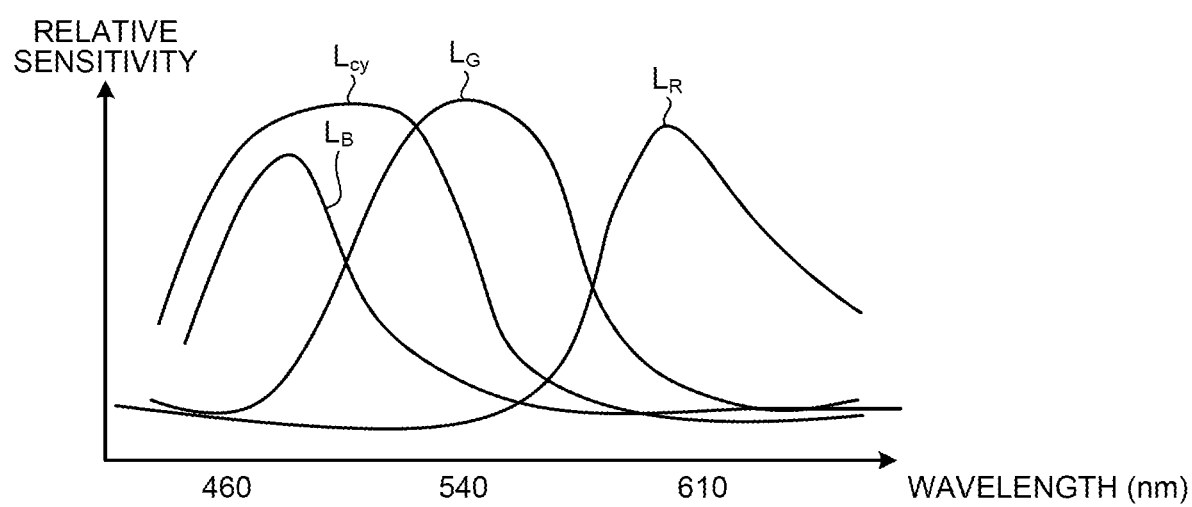
FIG. 40 is a diagram that schematically illustrates the sensitivity and the wavelength bandwidth of each filter.

FIG. 40 is a diagram that schematically illustrates the sensitivity and the wavelength bandwidth of each filter. In FIG. 40, the horizontal axis represents the wavelength (nm), and the vertical axis represents the sensitivity. Moreover, in FIG. 40, the curved line $L_B$ indicates the wavelength bandwidth of the blue color, the curved line $L_G$ indicates the wavelength bandwidth of the green color, the curved line $L_R$ indicates the wavelength bandwidth of the red color, and a curved line $L_{Cy}$ indicates the wavelength bandwidth of the cyan color.

As indicated by the curved line $L_{Cy}$ illustrated in FIG. 40, the cyan filters Cy transmit the light having the wavelength bandwidth of the blue color and the light having the wavelength bandwidth of the green color.

Configuration of Imager

Given below is the explanation of a configuration of an imager having the color filter 61E formed on the light receiving surface thereof. FIG. 41 is a diagram that schematically illustrates a layout of an imager 244E.

In the imager 244E illustrated in FIG. 41, the imaging pixels 70 are arranged as a two-dimensional matrix, and the phase difference pixels 71 are arranged at predetermined intervals and in place of the imaging pixels 70. More particularly, in the imager 244E, one right-opening pixel 71L or one left-opening pixel 71R is disposed in place of one of the two Cy pixels included in one filter unit U2. Moreover, in the horizontal direction of the imager 244E, either the right-opening pixels 71L or the left-opening pixels 71R are disposed in every second filter unit U2. Furthermore, in the vertical direction of the imager 244E, the right-opening pixels 71L and the left-opening pixels 71R are alternately disposed in every second filter unit U2. Meanwhile, the placement of the right-opening pixels 71L and the left-opening pixels 71R can be changed as appropriate.

The imager 244E configured in the manner explained above performs the ranging operation in an identical manner to the first to third embodiments.

According to the fifth embodiment described above, in an identical manner to the first to third embodiments, the accuracy of the ranging calculation can be enhanced.

First Modification Example of Fifth Embodiment

Configuration of Imager

Figure 42:
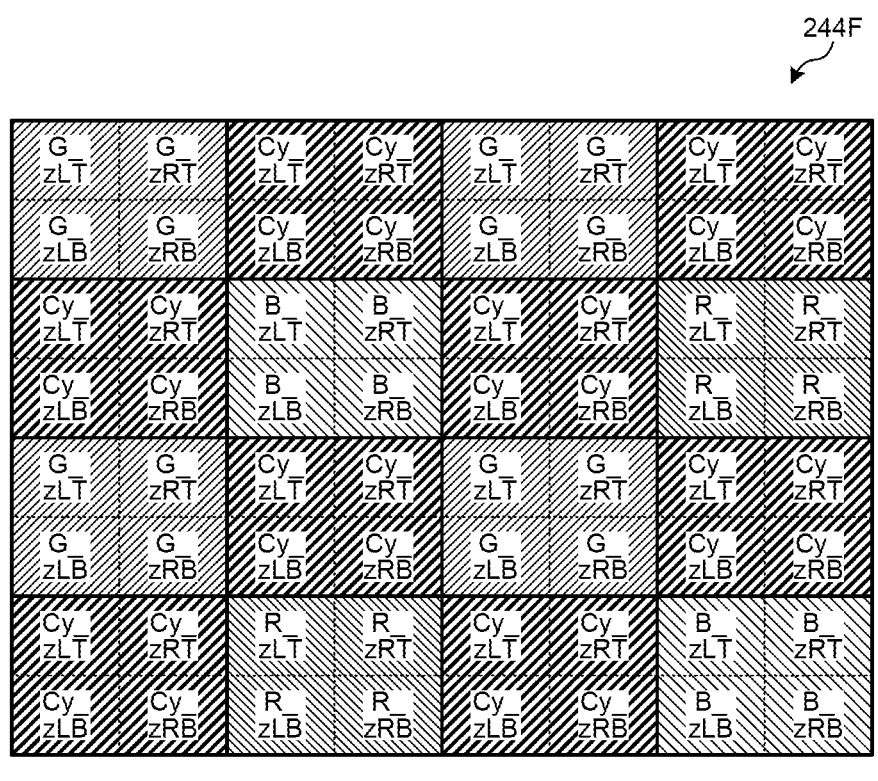
FIG. 42 is a diagram that schematically illustrates a layout of the imager according to a first modification example of the fifth embodiment.

Given below is the explanation of a first modification example of the fifth embodiment. FIG. 42 is a diagram that schematically illustrates a layout of the imager according to the first modification example of the fifth embodiment.

In an imager 244F illustrated in FIG. 42, the phase difference pixels 72 according to the fourth embodiment are arranged as a two-dimensional matrix; the four light receiving portions 721 to 724 are configured as single unit pixels; and any one of the filters of the color filter 61E is arranged on the light receiving surface of each of the four unit pixels. Meanwhile, in FIG. 42, the pixels in which the cyan filter Cy is arranged are referred to as "Cy_zLT", "Cy_zRT", "Cy_zRB", and "Cy_zLB" in the clockwise direction with reference to the top left pixel.

Ranging Operation

Figure 43:
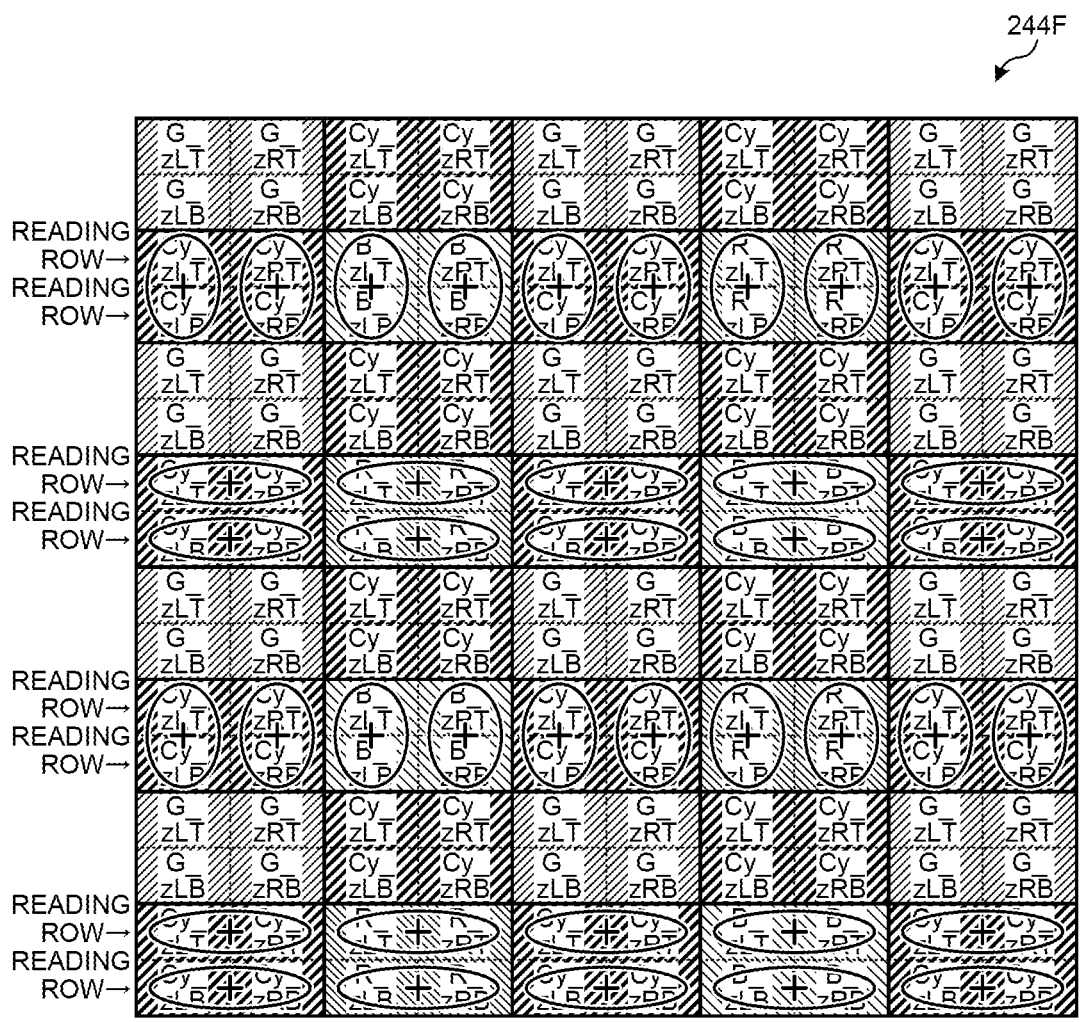
FIG. 43 is a diagram that schematically illustrates a method for reading the imager when the light source device emits light having the wavelength bandwidth of a short wavelength.

The following explanation is given about the overview of the method for reading from the imager 244F during the ranging operation performed in the endoscope system 1 that includes the imager 244F. FIG. 43 is a diagram that schematically illustrates the method for reading the imager when the light source device 3 emits light having the wavelength bandwidth of a short wavelength.

As illustrated in FIG. 43, at the point of time of rising of the ranging trigger due to the input of a ranging signal from the operating unit 22 or the input unit 52, the driving control unit 544 controls the illumination control unit 33; and, when the light source device 3 emits the B light having a short wavelength, controls the imaging control unit 65 and, in the odd-numbered rows among the reading rows in the imager 244F, adds the pixel signals of the left-side pixels and adds the pixel signals of the right-side pixels. Moreover, as a result of controlling the imaging control unit 65, in the even-numbered rows among the reading rows in the imager 244F, the driving control unit 544 adds the pixel signals of the upper-side pixels and adds the pixel signals of the lower-side pixels. More particularly, as a result of controlling the imaging control unit 65, in the odd-numbered rows among the reading rows in the imager 244F, the driving control unit 544 adds the pixel signals of the left-side pixels (i.e., Cy_zLT+Cy_zLB or B_zLT+B_zLB) and adds the pixel signals of the right-side pixels (i.e., Cy_zRT+Cy_zRB or R_zRT+R_zRB). Moreover, as a result of controlling the imaging control unit 65, in the even-numbered rows among the reading rows in the imager 244F, the driving control unit 544 adds the pixel signals of the upper-side pixels (i.e., Cy_zLT+Cy_zRT or B_zLT+B_zRT) and adds the pixel signals of the lower-side pixels (i.e., Cy_zLB+G_zRB or Cy_zLB+B_zRB). Consequently, the arithmetic processing unit 542 performs cross ranging.

According to the first modification example of the fifth embodiment, the accuracy of the ranging calculation can be enhanced.

Figures 44, 45:
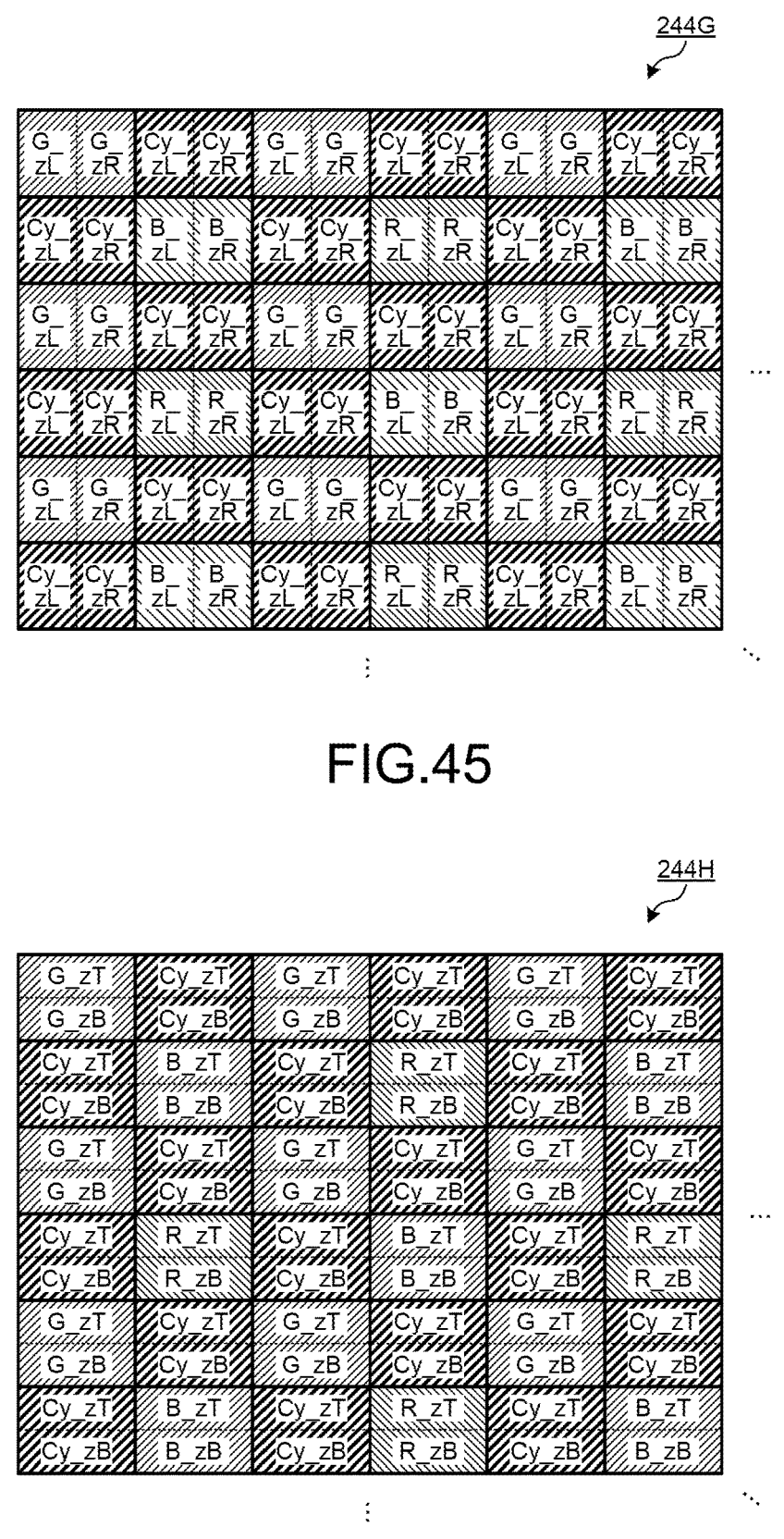

Meanwhile, in the first modification example of the fifth embodiment, the four light receiving portions 721 to 724 are treated as single unit pixels. Alternatively, as illustrated in an imager 244G in FIG. 44, a pair of right and left light receiving portions can be treated as a single unit pixel. Still alternatively, as illustrated in an imager 244H in FIG. 45, a pair of upper and lower light receiving portions can be treated as a single unit pixel.

Sixth Embodiment

Given below is the explanation of a sixth embodiment. In the sixth embodiment, the configuration of the endoscope system is identical to the endoscope system 1 according to the first embodiment, and only the ranging operation is different. More particularly, in the first embodiment, the degree of reliability of the ranging information is determined. In contrast, in the sixth embodiment, an approximation straight line is calculated based on a plurality of sets of ranging information, and the subject distance is estimated using the ranging calculation result corresponding to the distance having the highest degree of coincidence between the approximation straight line and the reference information. The following explanation is given about the ranging operation performed in the endoscope system according to the sixth embodiment. Meanwhile, the configuration identical to the endoscope system 1 according to the first embodiment is referred to by the same reference numerals, and the detailed explanation is not given again.

Ranging Operation

Figure 46:
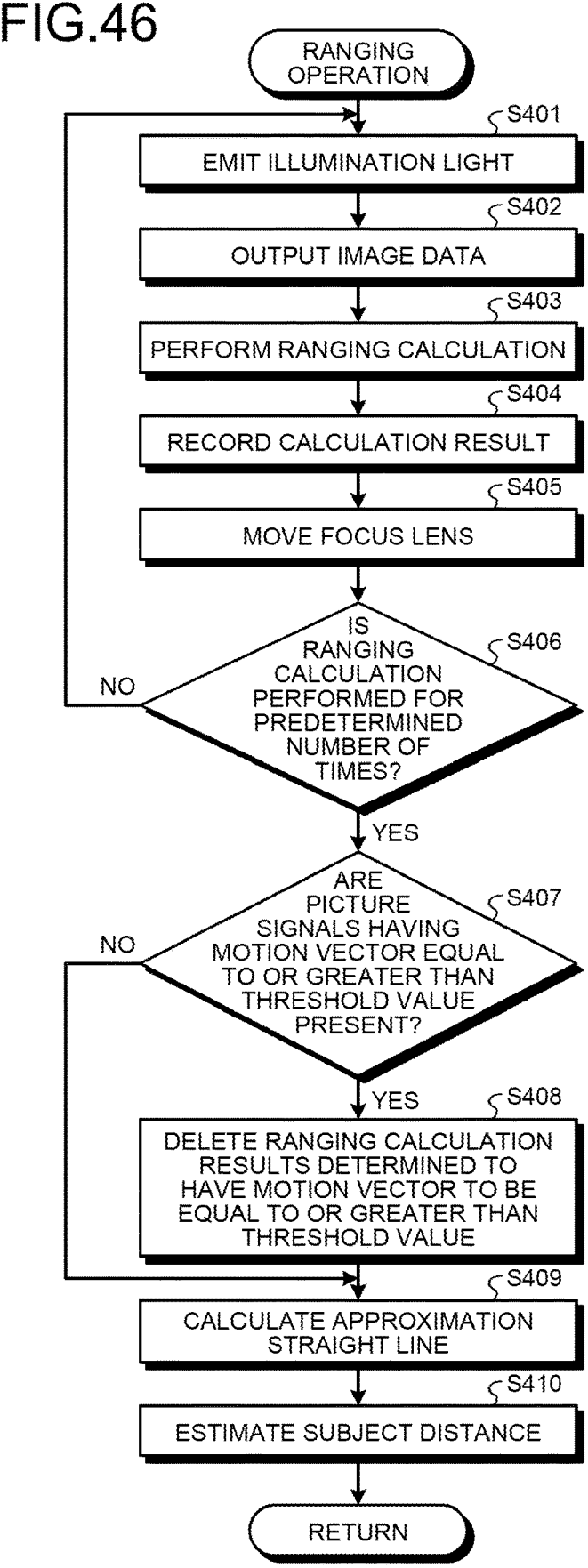
FIG. 46 is a flowchart for explaining the overview of a ranging operation performed in the endoscope system according to a sixth embodiment.
Figure 47:
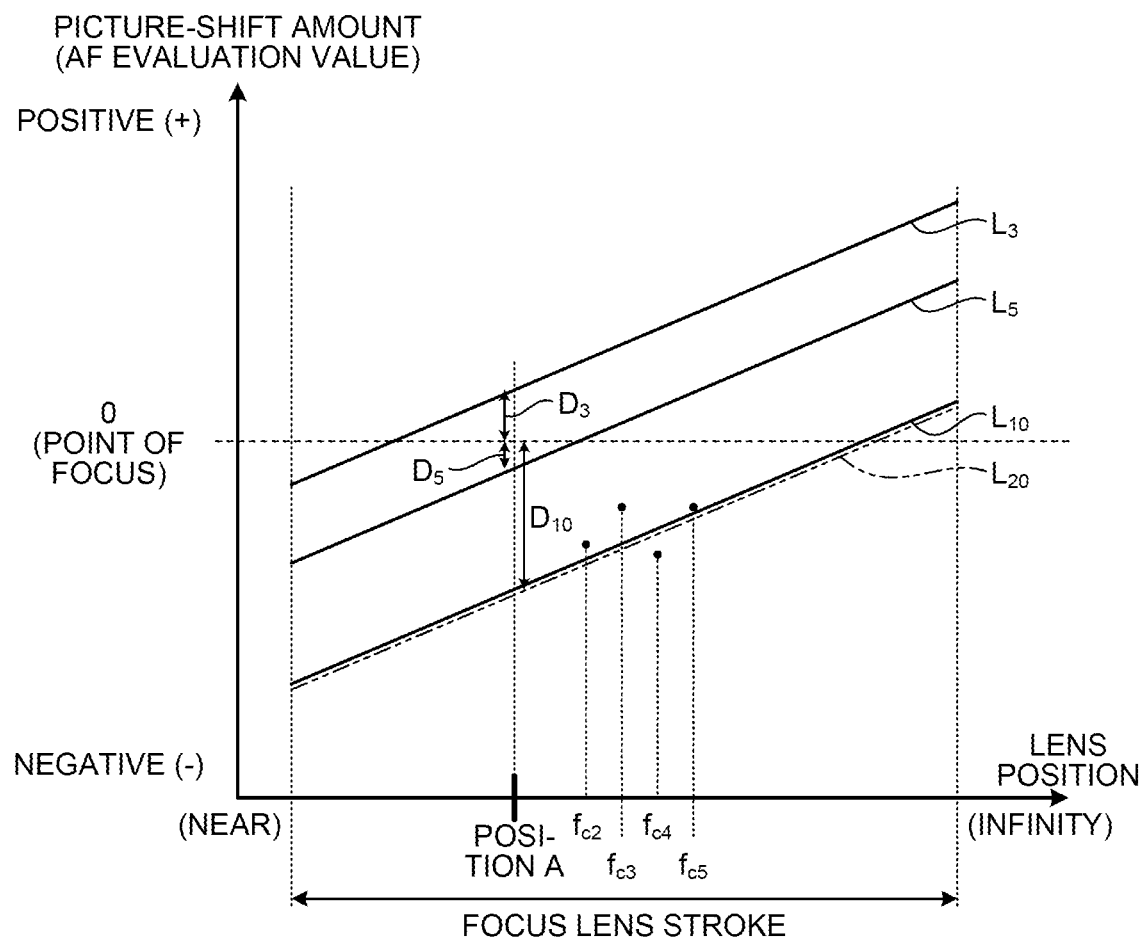
FIG. 47 is a diagram that schematically illustrates the overview of a determination method implemented by the determining unit according to the sixth embodiment.

FIG. 46 is a flowchart for explaining the overview of the ranging operation performed in the endoscope system according to the sixth embodiment. FIG. 47 is a diagram that schematically illustrates the overview of the determination method implemented by the determining unit 543. In FIG. 47, the horizontal axis represents the lens position of the focus lens 243a, and the vertical axis represents the picture-shift amount (the AF evaluation value). Moreover, in FIG. 47, a straight line $L_{20}$ indicates the approximation straight line that is based on the ranging calculation result obtained by the arithmetic processing unit 542. Moreover, the straight lines $L_3$, $L_5$, and $L_{10}$ are identical to those illustrated in FIG. 11 and indicate the picture-shift characteristics of the correspondence relationship among the subject distance to the subject, the picture-shift amount indicating ranging information correlated to the distance from the subject, and the focal position of the optical system 243. In FIG. 46, the operations performed from Step S401 to Step S408 correspond to the operations performed from Step S201 to Step S208, respectively, illustrated in FIG. 13.

At Step S409, the arithmetic processing unit 542 calculates an approximation straight line based on the reference information recorded in the reference information recording unit 532 and based on a plurality of sets of ranging calculation results (for example, the first ranging information and the second ranging information) recorded in the recording unit 53.

Then, the determining unit 543 estimates the subject distance using the ranging calculation result corresponding to the distance having the highest degree of coincidence between the approximation straight line calculated by the arithmetic processing unit 542 and the reference information recorded in the reference information recording unit 532 (Step S410). As illustrated in FIG. 47, firstly, the determining unit 543 determines the degree of coincidence of the approximation straight line $L_{20}$, which indicates the ranging calculation result attributed to the changes in the focal position of the optical system 243 based on the calculation results c2 to c4 obtained by the arithmetic processing unit 542, with each of the straight lines $L_3$, $L_5$, and $L_{10}$; and estimates the subject distance using the picture-shift characteristics having the highest degree of coincidence. In the case illustrated in FIG. 47, the determining unit 543 determines that the straight lines $L_{20}$ and $L_{10}$ have the highest degree of coincidence. Moreover, since the subject distance for the straight line $L_{10}$ is equal to 10 mm, the determining unit 543 estimates the subject distance to be equal to 10 mm. After the operation at Step S410 is performed, the system control returns to the main routine illustrated in FIG. 12.

According to the sixth embodiment described above, the determining unit 543 estimates the subject distance using the ranging calculation result corresponding to the distance having the highest degree of coincidence between the approximation straight line calculated by the arithmetic processing unit 542 and the reference information recorded in the reference information recording unit 532. As a result, the accuracy of the ranging calculation can be enhanced.

Other Embodiments

A plurality of constituent elements disclosed in the endoscope system according to the first to sixth embodiments of the disclosure can be appropriately combined and various embodiments can be made. For example, some of the constituent elements disclosed in the endoscope system according to the first to sixth embodiments of the disclosure can be deleted. Alternatively, the elements disclosed in the endoscope system according to the first to sixth embodiments of the disclosure can be appropriately combined.

Moreover, in the endoscope system according to the first to sixth embodiments of the disclosure, the term "unit" mentioned above can be read as "device" or "circuit". For example, a control unit can be read as a control device or a control circuit.

A computer program executed in the endoscope system according to the first to sixth embodiments of the disclosure is recorded as installable file data or executable file data in a compact disc read only memory (CD-ROM), a flexible disk (FD), a compact disc recordable (CD-R), a digital versatile disk (DVD), a USB medium (USB stands for Universal Serial Bus), or a flash memory.

Alternatively, the computer program executed in the endoscope system according to the first to sixth embodiments of the disclosure can be stored in a downloadable manner in a computer connected to a network such as the Internet.

Meanwhile, in the explanation of the flowchart given in the present written description, the context is explicitly illustrated using expressions such as "firstly", "then", and "subsequently". However, the sequence of operations required to implement the disclosure are not uniquely fixed by those expressions. That is, the sequence of operations illustrated in the flowcharts given in the present written description can be varied without causing contradiction.

According to the disclosure, it becomes possible to enhance the accuracy of the ranging calculation.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control device comprising: a processor comprising at least one hardware component, the processor being configured to
obtain, in an endoscope device that includes
an optical system configured to form an image of a subject, and
an imager that includes a phase difference pixel configured to generate a picture signal for generating ranging information correlated to distance from the subject,
a first picture signal generated by the phase difference pixel when the optical system has a first optical position, and a second picture signal generated by the phase difference pixel when the optical system has a second optical position,
calculate first ranging information based on the first picture signal,
calculate second ranging information based on the second picture signal,
estimate a first subject distance corresponding to the first ranging information based on reference information indicating correspondence relationship among a distance between the subject and the imager, information indicating focal position of the optical system, and the ranging information, the first ranging information, and information indicating the first focal position,
estimate ranging information corresponding to the second focal position based on the estimated first subject distance, information indicating the second focal position, and the reference information,
perform arithmetic processing to determine degree of reliability of the first ranging information based on the estimated ranging information corresponding to the second focal position and based on the second ranging information, and
output a result of the arithmetic processing,
wherein the processor is configured to perform the arithmetic processing to estimate a distance between the subject and the imager based on at least the first ranging information, the second ranging information, and the reference information.

2. The control device according to claim 1, wherein the processor is further configured to move the optical system along a light axis to change a focal position of the optical system from the first focal position to the second focal position.

3. The control device according to claim 1, wherein the processor is configured to cause the imager output the picture signal in response to an input of a ranging signal as an instruction for performing ranging.

4. The control device according to claim 3, wherein the processor is configured to cause the imager alternately output the picture signal and an image signal that is generated from a pixel other than the phase difference pixel in the imager.

5. The control device according to claim 4, wherein the processor is configured to either add picture signals of phase difference pixels on upper and lower sides in vertical direction to cause the imager output the added picture signals, or add picture signals of phase difference pixels on right and left sides in horizontal direction to cause the imager output the added picture signals.

6. The control device according to claim 1, wherein the processor is configured to
determine, from the picture signal, whether or not motion vector is equal to or greater than a threshold value, and exclude a pixel having the motion vector to be equal to or greater than the threshold value from among phase difference pixels, and determine the degree of reliability.

7. A control device comprising: a processor comprising at least one hardware component, the processor being configured to obtain, in an endoscope device that includes
an optical system configured to form an image of a subject, and
an imager that includes a phase difference pixel configured to generate a picture signal for generating ranging information correlated to distance from the subject,
a first picture signal generated by the phase difference pixel when the optical system has a first optical position, and a second picture signal generated by the phase difference pixel when the optical system has a second optical position, calculate first ranging information based on the first picture signal, calculate second ranging information based on the second picture signal, estimate a first subject distance corresponding to the first ranging information based on reference information indicating correspondence relationship among a distance between the subject and the imager, information indicating focal position of the optical system, and the ranging information, the first ranging information, and information indicating the first focal position, estimate ranging information corresponding to the second focal position based on the estimated first subject distance, information indicating the second focal position, and the reference information, perform arithmetic processing to determine degree of reliability of the first ranging information based on the estimated ranging information corresponding to the second focal position and based on the second ranging information, and output a result of the arithmetic processing, wherein the processor is further configured to change illumination light, which is directed onto the subject, from light having a first wavelength bandwidth to light having a second wavelength bandwidth to change focal position of the optical system from the first focal position to the second focal position.

8. The control device according to claim 7, wherein the processor is further configured to perform a control in which light emitted by a light source, which is capable of emitting narrow-bandwidth light having mutually different wavelength bandwidths as the first wavelength bandwidth and the second wavelength bandwidth, is changed from the light having the first wavelength bandwidth to the light having the second wavelength bandwidth.

9. The control device according to claim 8, wherein
the light source is configured to emit light having wavelength bandwidth of red color, light having wavelength bandwidth of green color, and light having wavelength bandwidth of blue color, and
when the phase difference pixel is placed at a position of a pixel on which a green filter transmitting light having wavelength bandwidth of green color is arranged, the processor is configured to cause the light source emit the light having wavelength bandwidth of green color in response to an input of a ranging signal as an instruction for performing ranging.

10. The control device according to claim 8, wherein
the light source is configured to emit light having wavelength bandwidth of red color, light having wavelength bandwidth of green color, light having wavelength bandwidth of blue color, and light having wavelength bandwidth of umber color, and
when the phase difference pixel is placed at a position of at least either a pixel on which a red filter transmitting light having wavelength bandwidth of red color is arranged, or a pixel on which a green filter transmitting light having wavelength bandwidth of green color is arranged, or a pixel on which a blue filter transmitting light having wavelength bandwidth of blue color is arranged, the processor is configured to cause the light source simultaneously emit both of the light having wavelength bandwidth of blue color and the light having wavelength bandwidth of green color or to cause the light source simultaneously emit both of the light having wavelength bandwidth of green color and the light having wavelength bandwidth of umber color in response to an input of a ranging signal as an instruction for performing ranging.

11. The control device according to claim 8, wherein
the light source is configured to emit light having wavelength bandwidth of red color, light having wavelength bandwidth of green color, light having wavelength bandwidth of blue color, and light having wavelength bandwidth of violet color, and
when the phase difference pixel is placed at a position of a pixel on which a cyan filter transmitting light having wavelength bandwidth of green color and transmitting light having wavelength bandwidth of blue color is arranged, the processor is configured to cause the light source alternately emit the light having wavelength bandwidth of green color and either the light having wavelength bandwidth of blue color or the light having wavelength bandwidth of violet color in response to an input of a ranging signal as an instruction for performing ranging.

12. The control device according to claim 8, wherein
the phase difference pixel includes a plurality of light receiving portions configured to receive light,
the imager includes a color filter including filter units that are placed on a plurality of pixels such that each filter unit corresponds to predetermined pixels of the plurality of pixels, the filter unit being made of a blue filter, a red filter, and two green filters,
the phase difference pixel is one of phase difference pixels arranged as a two-dimensional matrix in the imager,
the light source is configured to emit light having wavelength bandwidth of red color, light having wavelength bandwidth of green color, light having wavelength bandwidth of blue color, and light having wavelength bandwidth of umber color,
when the light source is made to emit the light having wavelength bandwidth of blue color, the processor is configured to cause the imager output the picture signal from only horizontal lines of the imager in which the blue filter and the green filter are placed, and
when the light source is made to emit the light having wavelength bandwidth of red color, the processor is configured to cause the imager output the picture signal from only horizontal lines of the imager in which the red filter and the blue filter are placed.

13. An endoscope system comprising:
an endoscope device; and
a control device to which the endoscope device is connected, and that includes a processor comprising at least one hardware component, wherein
the endoscope device includes
an optical system configured to form an image of a subject, and
an imager that includes a phase difference pixel configured to generate a picture signal for generating ranging information correlated to distance from the subject, and
the processor is configured to
obtain a first picture signal generated by the phase difference pixel when the optical system has a first optical position, and a second picture signal generated by the phase difference pixel when the optical system has a second optical position,
calculate first ranging information based on the first picture signal,
calculate second ranging information based on the second picture signal,
estimate a first subject distance corresponding to the first ranging information based on reference information indicating correspondence relationship among a distance between the subject and the imager, information indicating focal position of the optical system, and the ranging information, the first ranging information, and information indicating the first focal position,
estimate ranging information corresponding to the second focal position based on the estimated first subject distance, information indicating the second focal position, and the reference information,
perform arithmetic processing to determine degree of reliability of the first ranging information based on the estimated ranging information corresponding to the second focal position and based on the second ranging information, and
output a result of the arithmetic processing,
wherein the processor is configured to perform the arithmetic processing to estimate a distance between the subject and the imager based on at least the first ranging information, the second ranging information, and the reference information.

14. A control method implemented by a processor comprising at least one hardware component, the control method comprising:
obtaining, in an endoscope device that includes
an optical system configured to form an image of a subject, and
an imager that includes a phase difference pixel configured to generate a picture signal for generating ranging information correlated to distance from the subject,
a first picture signal generated by the phase difference pixel when the optical system has a first optical position, and a second picture signal generated by the phase difference pixel when the optical system has a second optical position,
calculating first ranging information based on the first picture signal,
calculating second ranging information based on the second picture signal,
estimating a first subject distance corresponding to the first ranging information based on reference information indicating correspondence relationship among a distance between the subject and the imager, information indicating focal position of the optical system, and the ranging information, the first ranging information, and information indicating the first focal position,
estimating ranging information corresponding to the second focal position based on the estimated first subject distance, information indicating the second focal position, and the reference information,
performing arithmetic processing to determine degree of reliability of the first ranging information based on the estimated ranging information corresponding to the second focal position and based on the second ranging information, and
outputting a result of the arithmetic processing,
wherein the processor is configured to perform the arithmetic processing to estimate a distance between the subject and the imager based on at least the first ranging information, the second ranging information, and the reference information.

* * * * *